United States Patent [19]
Alexander et al.

[11] Patent Number: 5,756,486
[45] Date of Patent: May 26, 1998

[54] METHOD FOR DOSING THERAPEUTIC COMPOUNDS

[75] Inventors: Petr Alexander, Foster City; Murty Arimilli, Fremont; Norbert Bischofberger, San Carlos; Michael J. M. Hitchcock, San Mateo, all of Calif.

[73] Assignee: Gilead Sciences, Inc., Foster City, Calif.

[21] Appl. No.: 708,596

[22] Filed: Sep. 5, 1996

Related U.S. Application Data

[62] Division of Ser. No. 597,005, Feb. 5, 1996, Pat. No. 5,591,851, which is a continuation of Ser. No. 193,341, Feb. 8, 1994, abandoned, which is a continuation-in-part of Ser. No. 123,483, Sep. 17, 1993, Pat. No. 5,656,745.

[51] Int. Cl.$^6$ .......................... A61K 31/675; C07F 9/02
[52] U.S. Cl. ................................................ 514/81; 544/244
[58] Field of Search ................................ 544/244; 514/81

[56] References Cited

U.S. PATENT DOCUMENTS

| | | | |
|---|---|---|---|
| 3,524,846 | 8/1970 | Moffatt et al. | 260/211.5 |
| 4,369,181 | 1/1983 | Miller et al. | 424/180 |
| 4,590,269 | 5/1986 | Prisbe et al. | 544/244 |
| 4,670,424 | 6/1987 | MacCoss et al. | 514/81 |
| 4,724,233 | 2/1988 | De Clercq et al. | 514/81 |
| 4,801,710 | 1/1989 | MacCoss et al. | 544/244 |
| 5,043,339 | 8/1991 | Beauchamp | 514/274 |
| 5,047,533 | 9/1991 | Reist et al. | 544/244 |
| 5,142,051 | 8/1992 | Holy et al. | 544/244 |
| 5,208,221 | 5/1993 | Kim et al. | 514/81 |
| 5,247,085 | 9/1993 | Harnden et al. | 544/244 |
| 5,386,030 | 1/1995 | Kim et al. | 544/243 |
| 5,391,723 | 2/1995 | Priest | 536/23.1 |
| 5,495,006 | 2/1996 | Climie et al. | 536/24.1 |

FOREIGN PATENT DOCUMENTS

| | | |
|---|---|---|
| 0 206 459 | 12/1986 | European Pat. Off. . |
| 0 253 412 | 1/1988 | European Pat. Off. . |
| 0 269 947 B1 | 6/1988 | European Pat. Off. . |
| 0 319 228 A3 | 11/1988 | European Pat. Off. . |
| 0 343 133 A1 | 11/1989 | European Pat. Off. . |
| 0 369 409 A1 | 5/1990 | European Pat. Off. . |
| 0 398 231 A2 | 11/1990 | European Pat. Off. . |
| 0 404 296 A1 | 12/1990 | European Pat. Off. . |
| 0 405 748 A1 | 1/1991 | European Pat. Off. . |
| 0 479 640 A2 | 9/1991 | European Pat. Off. . |
| 0 465 297 A1 | 1/1992 | European Pat. Off. . |
| 0 468 119 A1 | 1/1992 | European Pat. Off. . |
| 0 468 866 A1 | 1/1992 | European Pat. Off. . |
| 0 481 214 A1 | 4/1992 | European Pat. Off. . |
| 0 494 370 A1 | 7/1992 | European Pat. Off. . |
| 0 531 597 A1 | 3/1993 | European Pat. Off. . |
| 0 632 048 A1 | 6/1994 | European Pat. Off. . |
| 0 369 409 B1 | 1/1995 | European Pat. Off. . |
| 41 38 584 | 5/1993 | Germany . |
| 1243214 | 8/1971 | United Kingdom . |
| WO 88/05438 | 7/1988 | WIPO . |
| WO 91/19721 | 12/1991 | WIPO . |
| WO 92/01698 | 2/1992 | WIPO . |
| WO 92/09611 | 6/1992 | WIPO . |
| WO 92/13869 | 8/1992 | WIPO . |
| WO 94/03466 | 2/1994 | WIPO . |
| WO 94/03467 | 2/1994 | WIPO . |

OTHER PUBLICATIONS

Alexander et al., Collect Czech Chem Commun, 59:1853 (1994).

Andrei et al. "Comparative Activity of Selected Antiviral Compounds against Clinical Isolates of Human Cytomegalovirus," Eur J Clin Microbiol Infect Dis 10(12):1026–1033 (1991).

Bai et al. "Structural Specificity of Mucosal–Cell Transport and Metabolism of Peptide Drugs: Implication for Oral Peptide Drug Delivery," Pharm Res 9:969–979 (1992).

Barnard et al. "Selective inhibition of cytomegaloviruses by 9–(3'–ethylphosphono–1'–hydroxymethyl–1'–propyloxymethyl)guanine," Antiviral Res 22:77–89 (1993).

Beres, "Synthesis and Antitumor and Antiviral Properties of 5–Halo–and 5–(Trifluoromethly)–2'–deoxyuridine 3', 5'–Cyclic Monophosphates and Neutral Triesters," J Med Chem 29:1243–1249 (1986).

Bronson et al. "Synthesis and Biological Activity of Carbocyclic Derivatives of the Potent Antiviral Agent 9–[2–(Phosphonomethoxy)Ethyl]Guanine (PMEG)," Bioorg Med Chem Lett 2:685–690 (1992).

Colla et al. "Synthesis and Antiviral Activity of Water–Soluble Esters of Acyclovir [9–[(2–Hydroxyethoxy)methyl]guanine]," J Med Chem 26:602–604 (1983).

Curley et al. "Synthesis and anti–HIV evaluation of some phosphoramidate derivatives of AZT: studies on the effect of chain elongation on biological activity,"Antiviral Res 14:345–356 (1990).

Davies et al. "2'–Nor'2'–deoxyguanosine is an effective therapeutic agent for treatment of experimental herpes keratitis," Antiviral Res 7:119–125 (1987).

Duke et al., "In vitro and in vivo activities of phosphate derivatives of 9–(1, 3–dihydroxy–2–propoxymethyl)–guanine against cytomegaloviruses," Antiviral Res 6:299–308 (1986).

Engel, R., "Phosphonates as Analogues of Natural Phosphates," Chem Rev 77(3):349–367 (1977).

(List continued on next page.)

*Primary Examiner*—Mukund J. Shah
*Assistant Examiner*—Brenda Coleman
*Attorney, Agent, or Firm*—Max D. Hensley

[57] ABSTRACT

The internally cyclized congeners of hydroxy-substituted nucleotide analogues have been found to exhibit substantially lower toxicity in vivo than their uncyclized analogues, while retaining essentially the same antiviral activity. This was unexpected because the prior art suggested that the cyclic analogues offered no significant advantages in respect to toxicity. This finding permits the administration of much greater doses of the cyclic congeners than otherwise would have been possible and allows the clinician to omit toxicity ameliorating interventions. Novel compounds are provided for use in the method of this invention. Novel methods for the preparation of these compounds also are provided.

6 Claims, No Drawings

OTHER PUBLICATIONS

Farquhar et al, "Biologically Reversible Phosphate–Protective Groups," J Pharm Sci 72:324–325 (1983).

Farrow et al, "Synthesis and Biological Properties of Novel Phosphotriesters: A New Approach to the Intrduction of Biologically Active Nucleotides into Cells," J Med Chem 33:1400–1406 (1990).

Feng et al, "Combined treatment with 2'–nor–cGMP and ganciclovir against cytomegalovirus infection in a guinea pig model," Antiviral Res 19:193–206 (1992).

Field et al, "Efficacy of 2'–nor–cyclicGMP in treatment of experimental herpes virus infections," Antiviral Res 6:329–341 (1986).

Freed et al, "Evidence for Acyloxymethyl Esters of Pyrimidine 5'–Deoxyribonucleotides as Extracellular Sources of Active 5'–Deoxyribonucleotides in Cultured Cells," Biochem Pharm 38:3193–3198 (1989).

Freeman et al, "3'–Azido–3', 5'–dideoxythymidine–5'–methylphosphonic Acid Diphosphate: Synthesis and HIV–1 Reverse Transcriptase Inhibition," J Med Chem 35:3192–3196 (1992).

Gabrielsen et al, "Synthesis and In Vivo Anti–RNA–Viral Evaluation of a Phosphoramidate Derivative of 6–Azauridine; Orotidylic Acid Decaroboxylase Inhibitors, Pyrazofurin and 6–Azauridine; and 2–Thio–6–azauridine and its Triacetate," Antiviral Res 17(1):149 (1992).

Gumport et al, "Structure of the DNA Ligase–Adenylate Intermediate: Lysine (epsilon–amino)–Linked Adenosine Monophosphoramidate," Proc Natl Acad Sci 68(10):2559–2563 (1971).

Harnden et al, "Synthesis and Antiviral Activity of 9–Alkoxypurines. 1.9–(3–Hyroxypropoxy)–and 9–[3–Hydroxy–2–(hydroxymethyl)propoxy]purines," J Med Chem 33:187–196 (1990).

Ho et al, "Intracellular Metabolism of the Antiherpes Agent (S)–1–[3–Hydroxy–2–(phosphonylmethoxy)propyl]cytosine," Mol Pharm 41:197–202 (1992).

Holy et al, "Acyclic nucleotide analogues: synthesis, antiviral activity and inhibitory effects on some cellular and virus–encoded enzymes in vitro," Antiviral Res 13:295–312 (1990).

Holy et al, "Synthesis of (3–Hydroxy–2–Phosphonylmethoxypropyl) Derivatives of Heterocyclic Bases," Collect Czech Chem Commun 54:2470–2501 (1989).

Jahne et al, "Preparation of Carbocylic Phosphonate Nucleosides," Tet Lett 33(37):5335–5338 (1992).

Juodka et al, "Synthesis of Diribonucleoside phospho–(P–>N)–Amino Acid Derivatives," Collect Czech Chem Commun 39:963–968 (1974).

Karkas et al, "Stereochemical considerations in the enzymatic phosphorylation and antiviral activity of acyclonucleosides. I. Phosphorylation of 2'–nor–2'–deoxyguanosine," Biochem Biophys Acta 911:127–135 (1987).

Keim et al, "Amphotericin B Methyl Ester Hydrochloride and Amphotericin B: Comparative Acute Toxicity," Science 179(4073):584–585 (1973).

Kim et al, "a Novel Synthesis of 1–OXA–HPMPA: A Potent Antiviral Agent Against Herpes Viruses," Tet Lett 33(1):pp. 25–28 (1992).

Kim et al, "Acyclic Purine Phosphonate Analogues as Antiviral Agents. Synthesis and Structure—Activity Relationships," J Med Chem 33:1207–1213 (1990).

Kim et al, "Synthesis and HIV Activity of Phosphonate Isosteres of D4T Monophosphate,"Bioorg Med Chem Lett 5(2):367–370 (1992).

Kraus, "New Phosphonate Analogues of 3'–thia–2', 3'–dideoxycytidine (BCH–189). Synthesis and Anti–HIV Evaluation.," Nucls & Nuclt 12(2):157–162 (1993).

Kumar et al., "Synthesis and Biological Evaluation of Some Cyclic Phosphoramidate Nucleoside Derivatives," J Med Chem 33:2368–2375 (1990).

Li et al, "Activity of (S)–1–(3–hydroxy–2–phosphonylmethoxypropyl)cytosine (HPMPC) against guinea pig cytomegalovirus infection in cultured cells and in guinea pigs," Antiviral Res 13:237–252 (1990).

McGuigan et al, "Phosphoramidate derivatives of AZT as inhibitors of HIV: studies on the carboxyl terminus," Antiviral Chem & Chemo 4(2):97–101 (1993).

McGuigan et al, "Synthesis and anti–HIV activity of some haloalkyl phosphoramidate derivatives of 3'–azido–3'deoxythymidine (AZT): potent activity of the trichloroethyl methoxyalaninyl compound," Antiviral Res 15:255–263 (1991).

Midoux, "Drug Targeting: Anti–HSV–1 Activity of Mannosylated Polymer–Bound 9–(2–Phosphonylmethoxyethyl Adenine," Biochem Biophys Res Comm 167(3):1044–1049 (1990).

Mukaiyama et al, "Synthesis of Oligothymidylates and Nucleoside Cyclic Phosphates by Oxidation—Reduction Condensation," J Am Chem Soc 94(24):8528–8532 (1972).

Nelson et al., J Am Chem Soc. 109:4058 (1987).

Nielsen et al, "Evaluation of Glycolamide Esters and Various Other Esters of Aspirin as True Aspirin Produgs," J Med Chem 32:727–734 (1989).

Orchin, "The Vocabulary of Organic Chemistry," p. 283 (1980).

Palu et al, "Cellular uptake of phosphonylmethoxykylpurine derivatives," Antiviral Res 16:115–119 (1991).

Reist et al, "Synthesis of Acyclonucleoside Phosphonates as Antiviral Agents Against Cytomegalovirus," Nucls & Nuclt 13(1–3):539–550 (1994).

Rosenberg et al, "Phosphonylmethoxyalkyl and Phosphonylalkyl Derivatives of Adenine," Collect Czech Chem Commun 53:2753–2777 (1988).

Rosenberg et al, "Synthesis of Potential Prodrugs and Metabolites of 9–(S)–(3–Hydroxy–2–Phosphonylmethoxypropyl)Adenines," Collect Czech Chem Commun 52:2792–2800 (1987).

Sastry et al, "Membrane–Permeable Dideoxyuridine 5'–Monophosphate Analogue Inhibits Human Immunodeficiency Virus Infection,"Mol Pharm 41:441–445 (1992).

Snoeck et al, "Antiviral activity of anti–cytomegalovirus agents (HPMPC, HPMPA) assessed by a flow cytometric method and DNA hybridization technique," Antiviral Res 16:1–9 (1991).

Snoeck et al, "New acyclic nucleoside phosphonate derivatives as inhibitors of human cytomegalovirus," 29th Interscience Conference on Antimicrobial Agents and Chemotherapy p. 327, Abstract No. 1334 (Sep. 17–20, 1989).

Srivastva et al, "Bioreversible Phosphate Protective Groups: Synthesis and Stability of Model Acyloxymethyl Phosphates," Bioorg Chem 12:118–129 (1984).

Starrett et al, "Synthesis and in vitro evaluation of a phosphonate prodrug: bis(pivaloyloxymethyl)9–(2–phosphonylmethoxyelthyl)adenine," Antiviral Res 19:267–273 (1992).

Starrett et al., "Synthesis, Oral Bioavailability Determination, and in vitro Evaluation of Prodrugs of the Antiviral Agent 9-[2-(Phosphonomethoxy)eth]adenine (PMEA)," J Med Chem 37:1857–1864 (1994).

Sundraralingam et al., "Stereochemistry of Nucleic Acids and Their Constituents. XXVII. The Crystal Structure of 5'-Methyleneadenosine 3',5'-Cyclic Monophosphate Monohydrate, a Biologically Active Analog of the Secondary Hormonal Messenger Cyclic Adenosine 3',5'-Monophospat . . . ," J Am Chem Soc 94(14):5070–5076 (1972).

Tolman et al, "2'-nor-cGMP: A seco-Cyclic Nucleotide with Powerful Anti-DNA-Viral Activity\," Biochem Biophys Res Comm 128(3):1329–1335 (1985).

Trost et al., Comprehensive Organic Synthesis, 2:777–778 (1991).

Wolff–Kugel et al, "Synthesis of New Carbocyclic Phosphonate Analogs of Dideoxypurine Nucleotides," Tet Lett 32(44):6341–6344 (1991).

Yu et al, "Synthesis and Antiviral Activity of Methyl Derivatives of 9-[2-(Phosphonomethoxy)ethyl]guanine," J Med Chem 35:2958–2969 (Aug. 7, 1992).

Bruice et al., "Hydrolysis of a Phosphate Diester by Simultaneous Carboxylate and Carboxyl Group Participation in a Rigid System with Kinetically Unfavorable Rotamers Frozen Out," J Am Chem Soc 117:3639–3640 (1995).

Charvet et al., "Inhibition of Human Immunodeficiency Virus Type 1 Replication by Phosphonoformate—and Phosphonoacetate—2',3'-Dideoxy-3'-thiacytidine Conjugates," J Med Chem 37:2216–2223 (1994).

Glazier et al., "Potent Topical Anti-Herpes Activity of a Lipophilic Phosphorus Prodrug for the Antiviral Agent PMEA," 8th International Conference on Antiviral Research, Santa Fe, NM p. A306–Poster (Apr. 23–28, 1995).

Jacobson et al., "Phase I Trial of Valaciclovir, the L–Valyl Ester of Acyclovir, in Patients with Advanced Human Immunodeficiency Virus Disease," Antimicro Ag & Chemo 38(7):1534–1540 (Jul. 1994).

Jones et al., "Minireview: nucleotide prodrugs," Antiviral Res 27:1–17 (1995).

Serafinowska et al., "Synthesis and in Vivo Evaluation of Prodrugs of 9-[2-(Phosphonomethoxy)ethoxy]adenine," J Med Chem 38:1372–1379 (1995).

Smee et al., "Potent Anti-Murine Cytomegalovirus Activity and Reduced Nephrotoxicity of Gabciclovir Cyclic Phosphonate," Antimicro Ag & Chemo 40(8):1964–1966 (Aug. 1996).

Xiong et al., "Kinetic Analysis of the Interaction of Cidofovir Diphosphate with Human Cytomegalovirus DNA Polymerase," Biochem Pharm 51:1563–1567 (1996).

METHOD FOR DOSING THERAPEUTIC COMPOUNDS

This is a divisional of application Ser. No. 08/597,005 filed on Feb. 5, 1996, now U.S. Pat. No. 5,591,851, which is a continuation of U.S. Ser. No. 08/193,341, filed Feb. 8, 1994, now abandoned, which is a continuation-in-part of U.S. Ser. No. 08/123,483, filed Sep. 17, 1993, now U.S. Pat. No. 5,656,745.

Cross-reference is made to related copending application U.S. Ser. No. 08/612,889.

This invention relates to methods and compounds for the treatment of viral infections, including prophylaxis. In particular it is concerned with the management of kidney toxicity by selection of therapeutic dosages of antiviral compounds.

A number of antiviral compounds are known that are characterized by a phosphonate group linked to a nucleotide base via a hydroxy-substituted cyclic or acyclic linking moiety, wherein the hydroxy group is joined by 4 atoms (typically as alkyl or alkoxyalkyl chains) to the phosphorus atom and the phosphorus atom is bonded to a methylene group of the cyclic or acyclic linking moiety. These hydroxy-substituted nucleotide analogues (herein, "HSNA"s) include the compounds of structures (I)–(VII) below. Structure (I) compounds are disclosed in EP 369,409 and/or U.S. Ser. No. 08/110,841 (pending):

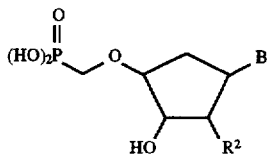

wherein B is a heterocyclic group having at least 1 nitrogen heteroatom and up to 3 additional heteroatoms selected from nitrogen, oxygen and sulfur, said heterocyclic group being connected through a nitrogen heteroatom thereof, and $R^2$ is hydrogen, hydroxy, fluorine, chlorine, bromine, amino, or an organic substituent having 1–5 carbon atoms and selected from acyloxy, alkoxy, alkylthio, alkylamino or dialkylamino.

Structure (II) and (III) compounds are disclosed in EP 398,231:

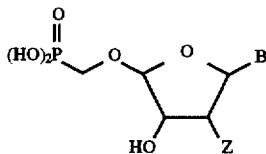

wherein Z is hydrogen or $C_1$–$C_6$ alkyl and B is a 9-substituted purine or 1-substituted pyrimidine base; and

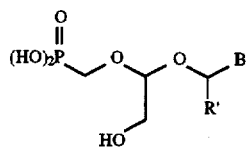

wherein R' is hydrogen, $C_1$–$C_6$ alkyl or hydroxyalkyl with 1–6 carbon atoms, and B is a 9-substituted purine or 1-substituted pyrimidine base.

Barnard et al. ("Antiviral Research" 22:77–89 [1993]) disclose HSNA compounds of structure (IV):

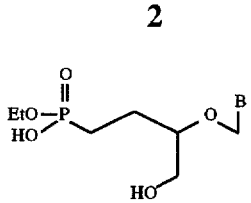

wherein B is guanin-9-yl.

U.S. Pat. No. 5,208,221 discloses HSNA compounds of structure (V):

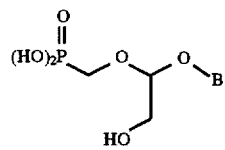

wherein B is a 9-substituted purine or 1-substituted pyrimidine base.

U.S. Pat. No. 5,247,085 discloses HSNA compounds of structure (VI):

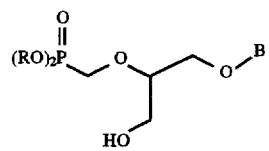

wherein R is H, $C_1$–$C_6$ alkyl, or optionally substituted phenyl and B is one of a group of defined purin-9-yl bases.

Other well-known HSNAs include certain 3-hydroxy-2-(phosphonomethoxy)propyl analogues of nucleotide bases (herein, "HPMPB") of structure (VII):

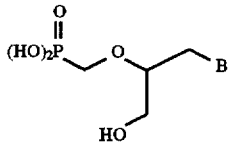

wherein B is a pyrimidin-1-yl, pyrimidin-3-yl, purin-3-yl, purin-7-yl or purin-9-yl residue, or the deaza, aza or deaza-aza analogues thereof. These compounds are active against DNA viruses. The principal members of the HPMP class are the compounds of structure (VII) in which B is cytosin-1-yl (herein, "HPMPC") or adenin-9-yl (herein, "HPMPA"). The (S) isomers are preferred. See U.S. Pat. Nos. 5,142,051 and 4,724,233.

It is known to internally cyclize certain HSNA compounds. cHPMPBs are the internally cyclized congeners of the corresponding HPMPB and have structure (VIIa):

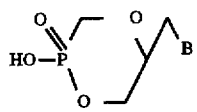

wherein B is as defined in structure (VII). Two examples of the compounds of structure (VIIa) are known: cHPMPA and cHPMPC (U.S. Pat. No. 4,724,233 and Ho et al., "Mol. Pharmacology" 41:197–202, [1992]). The (S) enantiomer of cHPMPC bears the IUPAC name 1-[((S)-2-hydroxy-2-oxo-1,4,2-dioxaphosphorinan-5-yl)methyl] cytosine (CAS Reg. No. 127757-45-3).

In addition, the internally cyclized analogues of the compounds of structures (II) and (III) (EP 398,231) and (VI) (U.S. Pat. No. 5,247,085) are known. They have the structures (IIa), (IIIa) and (VIa):

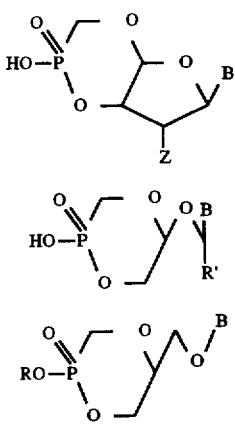

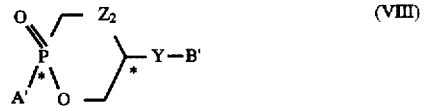

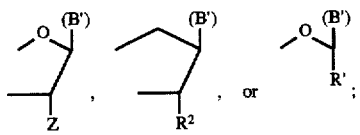

wherein Z, R, R' and B are defined above in structures (II), (III) and (VI).

HPMPC has been extensively studied and currently is in human clinical trials. Its cyclic congener has received comparatively little attention. However, cHPMPC has been reported to have activity against cytomegalovirus in human embryonic lung cells in vitro (Snoeck et al., "Antiviral Research" 16:1–9 [1991]). The Snoeck et al. data suggest that cHPMPC is less toxic than HPMPC, but less efficacious as well by approximately the same degree. In particular, Snoeck et al. reported that the micromolar cytotoxicities of cHPMPC and HPMPC were 720 and 360, respectively, by cell growth and 108 and 72, respectively, by radiothymidine incorporation. Holy et al. ("Antiviral Research" 13:295–312 [1990]) reported similar in vitro cell culture data. See also Snoeck et al., "Int. Congr. Ser. Excerpta Med.," 978 (Prog. Cytomegalovirus Res.) 337–340 (1991) and Holy et al., "Coll. Czech. Chem. Commun." 54(a): 2470–2501 (1989).

Li et al. have reported that HPMPC is nephrotoxic in guinea pigs (see "Antiviral Research" 13:237–252 [1990]), and nephrotoxicity is the limiting toxicity in human clinical trials of HPMPC. Human nephrotoxicity is ameliorated by concomitant administration of probenecid and by giving fluids prior to HPMPC administration (hydration). In contrast to the extensive studies of HPMPC, the published literature is believed to be devoid of any animal studies of efficacy or toxicity of cHPMPC.

It is an object of this invention to enlarge the therapeutic window for HSNAs by supplying them in a form that is less toxic in vivo while substantially retaining the antiviral activity of the HSNA. In addition, it is an object of the invention to reduce or eliminate the practice of hydration or probenecid administration during a course of HPMPC therapy and to minimize the need to withdraw patients from HSNA treatment due to the development of kidney toxicity. An additional object of this invention is to facilitate non toxic increases in the dose, frequency and length of administration of HSNAs. It is a further object of this invention to provide novel internally cyclized derivatives of certain HSNAs. Another object of this invention is to provide intermediate forms of HSNAs having oral bioavailability, reduced toxicity and greater efficacy, together with novel methods for their manufacture.

SUMMARY OF THE INVENTION

The objects of this invention are accomplished by administering to a subject an antivirally effective, non-cytotoxic dose of cHSNA which is in excess of the maximum non-cytotoxic dose for the corresponding uncyclized HSNA. In certain embodiments the maximum non-cytotoxic dose is defined in terms of the maximum non-nephrotoxic dose. In preferred embodiments, particularly where the HSNA is HPMPC, the cHSNA dose is in excess of 2 times the HSNA maximum non-cytotoxic dose. In additional embodiments an antivirally effective course of therapy of cHPMPC or other cHSNA is administered without probenecid and/or hydration.

The cHSNAs to be used in the practice of this invention have structure (VIII)

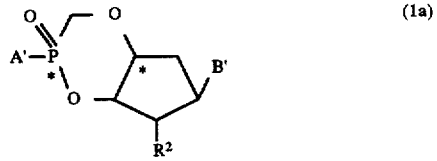

wherein $Z_2$ is oxygen or methylene, Y is —$CH_2$—, —$OCH_2$—, —O—

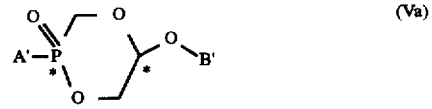

Z, R', and $R^2$ are defined above, A' is OH or A, A is an amidate or ester, the stereochemistry of the carbon and phosphorus atoms denoted with the asterisks independently are (S), (R) or (R,S), the orientation of the Y groups is shown by (B'), and B' is an unsubstituted nitrogen-, or nitrogen and sulfur-containing heterocyclic ring structure or such ring structure substituted with from 1 to 3 substituents independently selected from oxo, hydroxy, amino, fluoro, chloro, bromo, iodo, $C_1$–$C_9$ haloalkyl (1–3 halo), $C_1$–$C_9$ alkyl, $C_2$–$C_9$ alkenyl, $C_2$–$C_9$ haloalkenyl, $C_1$–$C_9$ alkoxy, $C_2$–$C_9$ thioalkenyl, $C_1$–$C_9$ alkylthiol, amino $C_1$–$C_9$ alkyl, amino $C_3$–$C_4$ alkenyl, amino $C_3$–$C_4$ alkynyl, cycloamino $C_2$–$C_5$ alkyl, thio $C_1$–$C_9$ alkyl, $C_1$–$C_9$ hydroxyalkyl, $C_1$–$C_3$ alkoxy, $C_1$–$C_4$ alkyl, acylamine, thiol, =S, or =N—$NH_2$.

In other embodiments of the invention, novel compounds are provided which have the structures (Ia) and (Va):

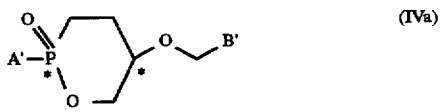

wherein * designates (S), (R) or (R,S) configuration, and B', $R^2$ and A' are defined above, together with the salts thereof. Structure (Va) is

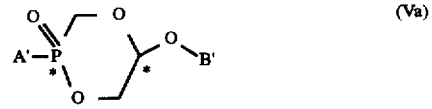

wherein * and A' and B' are defined above, together with the salts thereof.

Also useful in this invention are compounds of structure (IVa)

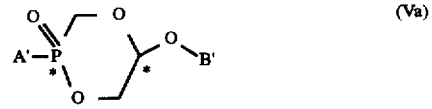

wherein * and A' and B' are defined above, together with the salts thereof. In each of (Ia) and (Va), the carbon atom * chiral center preferably is (S); in (IVa) it preferably is (R).

This invention also includes the novel uncyclized counterparts of the foregoing cHSNAs of structure (VIII), which will differ from the known uncyclized forms in the choice of base and/or choice of A' (the A' group(s) of the uncyclized counterparts will be OH, or monosubstituted or disubstituted with A, wherein the A groups are the same or different). Hereby excluded from the scope of this invention are any uncyclized HSNAs that are not novel and unobvious over their prior art uncyclized counterparts.

DETAILED DESCRIPTION OF THE INVENTION

HPMPC is the HSNA for which the greatest human clinical experience is available. For the most part, HPMPC has been administered once or twice weekly for 4 weeks, and patients completing the 4 week study without evidence of drug-related toxicity continued with weekly therapy. HIV-infected patients with asymptomatic CMV infection of urine and semen have tolerated doses of HPMPC at 0.5, 1.0 and 1.5 mg/kg for 4 weeks without evidence of significant HPMPC-related clinical or laboratory toxicity.

Patients treated at the highest dose levels previously studied (5.0 mg/kg twice weekly and 3.0 or 10.0 mg/kg once weekly) developed evidence after as few as 1 or 2 doses for HPMPC-related nephrotoxicity manifested by proteinuria, glycosuria, and decreases in serum phosphate, uric acid, and bicarbonate consistent with renal proximal tubular cell injury. Two of five patients receiving 3.0 mg/kg once weekly developed Grade II nephrotoxicity (serum creatinine of $\geq 2.0$ mg/dL or 2+ proteinuria) following 6 and 14 doses of HPMPC, respectively. Two of five patients receiving 10.0 mg/kg once weekly of HPMPC developed evidence of persistent Grade IV nephrotoxicity following two doses. Both patients had evidence of non-oliguric renal insufficiency consistent with proximal tubular cell injury. Each of the above four patients displaying nephrotoxicity did not receive concomitant hydration during the antecedent HPMPC infusions. Persistent nephrotoxicity ($\geq$Grade II) has not been observed in patients receiving concomitant hydration with HPMPC.

Proteinuria, as measured by routine urinalysis, appears to be a sensitive early indicator of HSNA-related nephrotoxicity. Interruption of HPMPC treatment following the appearance of proteinuria has permitted the administration of systemic HPMPC without significant drug-related toxicity. Continued administration of HPMPC following the demonstration of proteinuria with or without serum creatinine elevation can result in prolonged and potentially irreversible renal insufficiency.

Identification of the sequence of urinalysis and serum chemistry abnormalities associated with HPMPC-related nephrotoxicity, as well as demonstration of prolonged anti-CMV effect, has led to modifications in the methods of HPMPC administration (Table 1). For example, interruption of HPMPC treatment following the appearance of $\geq 1+$ proteinuria has permitted the administration of systemic HPMPC without significant drug-related toxicity. Investigation of longer dosing intervals (one, two, and three weeks) has also been pursued. Additionally, as suggested by preclinical animal studies, concomitant administration of probenecid has been employed in an effort to block uptake of HPMPC by the proximal tubular cell of the kidney.

TABLE 1

Phase I/II HPMPC Regimens:
Dose - Refinements

| Dose (mg/kg) | Schedule | Hydration[1] |
|---|---|---|
| 3.0 + Probenecid[2] | q week | +/− |
| 5.0 + Probenecid | q week | +/− |
| 5.0 + Probenecid | q 2 weeks | +/− |
| 7.5 + Probenecid | q 3 weeks | +/− |

[1]Administered as one liter normal saline over approximately 45 minutes immediately prior to HPMPC infusion.
[2]Administered orally as 2 grams (3 h pre-HPMPC), 1 gram (2 h post-HPMPC), and 1 gram (8 h post-HPMPC) (total dose = 4 grams).

To date, 21 patients have received HPMPC with concomitant probenecid (8 patients at 3 mg/kg [range 2–11 doses]; 11 patients at 5 mg/kg [range 2–8 doses]; and 2 patients at 7.5 mg/kg [range 1–2 doses]). None of these patients have developed proteinuria.

Three of 21 patients developed evidence of allergic symptoms temporally related to probenecid administration. Each occurred after 3 to 4 consecutive weeks of treatment. Two of three developed pruritic maculopapular rashes responsive to antihistamine therapy, permitting continued administration. The third patient developed evidence of a systemic reaction including rash, nausea and headache. The contribution of other medications interacting with probenecid is uncertain at this time; however, as zidovudine (AZT) levels have been demonstrated to increase significantly when administered with probenecid, patients have been cautioned to withhold or reduce (e.g., 50 percent reduction) their AZT doses on days of probenecid administration. Thus, it is desirable to eliminate the use of probenecid in treatment with HPMPC.

The serious adverse events observed in these clinical studies are listed below (Table 2). The table includes all reported serious adverse events, whether or not they were felt to be related to HPMPC. As noted above, nephrotoxicity appears to be the major dose-limiting toxicity related to HPMPC administration. Additionally, neutropenia has been observed in these studies. It is noteworthy that this hematologic toxicity does not appear to be dose dependent. The frequency of neutropenia appears to be comparable with reported rates of neutropenia observed in similar patient populations studied in controlled clinical trials (i.e., patients with advanced HIV infection and CD4 cell count <100 cells/mm³ receiving concomitant antiretroviral therapies).

TABLE 2

Serious Adverse Events Associated with HPMPC Administration

| Body system | Preferred Term | No. of Patients[1] | Percent of Patients |
|---|---|---|---|
| Body as a Whole | asthenia | 1 | 1.6 |
| | allergic reaction (probenecid) | 1 | 1.6 |
| | infection (1 MAC & 1 PCP) | 2 | 3.3 |
| Cardiovascular System | aneurysm | 1 | 1.6 |
| Hemic and Lymphatic System | neutropenia ($\leq 750$ cells/mm³) | 7 | 11.5 |
| | neoplasm (lymphoma) | 1 | 1.6 |
| Special Senses | uveitis | 1 | 1.6 |
| Urogenital System | renal insufficiency (Cr $\geq$ 2 mg/dL) | 5 | 8.2 |

[1]Of 61 total patients who have received HPMPC.

In accordance with the results of preclinical animal studies, early clinical studies have identified nephrotoxicity as the major dose limiting toxicity of HPMPC. Similar dose limiting toxicity ultimately may be encountered with cHPMPC, but the animal studies described in the examples below clearly demonstrate that the therapeutic window for the cyclic form is much wider than for HPMPC. However, at elevated doses of cHPMPC, concomitant administration of agents with nephrotoxic potential should be avoided, if possible, and adherence to pre-cHPMPC dose examination of urinalysis and serum chemistries will minimize the potential for nephrotoxicity. Concomitant administration of hydration and probenecid at cHPMPC doses approaching nephrotoxicity may be nephroprotective, as is the case with HPMPC, although hydration is expected to be of greatest value at such elevated cHPMPC doses.

Animals receiving massive doses of HPMPC also developed evidence of bone marrow suppression and lymphoid depletion felt to be secondary to renal failure and limited clearance of the drug. While neutropenia has occurred in patients receiving HPMPC in early clinical studies, this has not been dose-dependent and may be unrelated to HPMPC. It is unclear whether similar effects will be encountered with cHPMPC, but the clinician would be advised to be alert for them.

Side effects associated with the administration of other antiviral medications include sensory and motor neuropathy, central nervous system depression and agitation, headaches, nausea, vomiting, diarrhea, pancreatitis, hepatotoxicity, oral ulcers, cutaneous reactions, marrow suppression, and nephrotoxicity. Any of these side effects are possible with cHPMPC.

Determination of Maximum Non-Cytotoxic Dosages of HSNA's; cHSNA Dosing

The term "maximum non-cytotoxic dose" (hereafter "MND") means the maximum molar quantitative amount of HSNA that can be administered to the subject in question without inducing a toxic response that, in the opinion of the ordinary reasonable clinician, would necessitate a reduction in dose of the HSNA or the withdrawal of the subject from treatment with the HSNA. The MND for a given subject will vary depending on a number of factors, including the pre-existing condition of the patient, (the MND will be lower if the patient already is demonstrating injury to an organ for which the HSNA is cytotoxic), the nature of the cytotoxicity (potentially life-threatening cytotoxicities, e.g. for organs such as kidney or liver, will lower the MND), the frequency of administration of the HSNA (giving the same dose of HSNA in dispersed doses as opposed to a bolus generally will lower the MND for the HSNA over a given period of time), the period that the subject has been on the HSNA (longer periods of therapy on HSNA generally will lower the MND for subsequent dosings) and the presence or absence of concomitant therapies that are expected to exacerbate or to ameliorate the expected cytotoxicity. It is possible with minimal experimentation to determine the MND for the ordinary subject, for example patients not bearing any unusual pre-existing conditions and not requiring coadministration of agents expected to exacerbate the HSNA cytotoxicity in question. This MND can be used to establish the initial dose for subsequent patients in the same cohort. In any case, the practice of monitoring and optimizing therapeutic dosing even in individual patients is a long standing and conventional practice, and it would not require any experimental effort outside that which is ordinarily undertaken by the clinician.

Frequently encountered HSNA cytotoxicities include skin irritation (when administered topically), punctal stenosis (when administered by opthalmic modes of delivery, such as eyedrops) and nephrotoxicity by systemic treatment as described above. cHSNAs are expected to exhibit substantially less of these cytotoxicities while still having essentially the same antiviral activity, thereby permitting the molar dose of cHSNA to exceed the MND of the corresponding HSNA. Since the antiviral activity of the cHSNA is essentially the same as the HSNA on an equimolar dose basis, administration of the cHSNA dose above the MND of the HSNA will greatly increase therapeutic antiviral activity.

Nephrotoxicity is the dose-limiting toxicity for many HSNAs, and is the current barrier to administration of larger doses of HPMPC by systemic routes. Accordingly, the MND for systemically-administered HPMPC is equivalent to its maximum non-nephrotoxic dose.

The term "non-nephrotoxic dose" means a systemic dose administered by a route, frequency and amount that fails to produce 2+ proteinuria as measured by urinalysis reagent strips. The "maximum non-nephrotoxic dose" means the greatest amount of HSNA by a given route and frequency that can be administered to a subject without producing 2+ proteinuria. The patient being treated may be exposed to nephrotoxic agents or have pre-existing kidney damage, in which case the maximum non-nephrotoxic dose in these patients will be lower than in most patients. On the contrary, supplemental therapies directed at ameliorating nephrotoxicity, e.g., administration of probenecid or adequate hydration, will cause the maximum non-nephrotoxic dose to be higher than in patients not receiving such therapies. Accordingly, the range of non-nephrotoxic doses will vary somewhat from patient-to-patient depending upon these and other factors known to the artisan. In general, one must take into account the condition of the patient, the distribution of the dosage over time, the amount of time the patient has been on drug, the administration route, the animal species being treated, the use of nephroprotective measures such as probenecid and hydration, and the concomitant administration of nephrotoxins. The maximum non-nephrotoxic dose for HPMPC for humans in the ordinary clinical setting generally is about 5 mg/kg weekly parenterally when administered with probenecid and hydration, or about 2 mg/kg weekly parenterally without probenecid and hydration. The maximum non-nephrotoxic doses of other HSNAs are determined by routine preclinical or clinical experiments well within the ordinary skill in the art as described above. A salient feature of this invention is that substantially the same or greater antivirally efficacy of an HSNA can be achieved with the same dosage of cyclic analogue of the HSNA, but with much less toxicity, in particular nephrotoxicity. This means that the minimum antivirally active, non-nephrotoxic dose of the cHSNA will be greater than the maximum non-nephrotoxic dose of the HSNA on a molar basis, all other therapeutic influences being essentially the same as noted above.

Since cHPMPC is substantially less toxic, but similarly efficacious compared to HPMPC, one can employ substantially greater systemic molar doses of cHPMPC than the maximum non-nephrotoxic dose of HPMPC and still not induce nephrotoxicity in patients. In most embodiments, the typical cHPMPC molar dosage will be greater than twice (on a molar basis) the HPMPC maximum non-nephrotoxic or non-cytotoxic dose, although it also may be 3, 4, 5, 6, 7, 8, 9, 10 times the maximum non-nephrotoxic or non-cytotoxic dose. In most circumstances, a cHPMPC dosage of greater than about 10 mg/kg/week administered parenterally to humans will be antivirally effective and non-nephrotoxic. However, dosages of about 15, 20, 25, 30, 35, 40, 45 or 50 mg/kg/week also may be suitable under the circumstances.

The greatest non-nephrotoxic dose of cHPMPC that can be used in humans is believed to be in the order of 50 mg/kg/week, but will vary based on the same parameters as the minimum dose, and may extend to 100 mg/kg/week.

One also needs to take into account whether the HSNA or cHSNA is an intermediate that is converted in vivo into the free acid, i.e., whether the phosphonate hydroxyl group(s) are unsubstituted or are substituted by A group(s). In general, the dosage of an intermediate form of cHSNA will be higher than that of the free hydroxyl HSNA, taking into account the bioavailability of the intermediate by oral intake and its greater molecular weight. The dosage of this invention for a given cHSNA intermediate is determined readily by assaying the proportion of free cHSNA generated in the plasma upon administration of the intermediate, generally by the oral route. The intermediate will be administered so as to emulate the desired cHSNA plasma concentration previously obtained by intravenous or other systemic administration routes. Analogous reasoning is applied to topical routes of administration, where the benchmark is the tissue concentration at the topical site of delivery. In an illustrative example of the foregoing principles, if the maximum non-nephrotoxic dose of the uncyclized HSNA by intravenous administration is 1 mg/kg/day, then the intravenous dose of the cHSNA will be greater than 1 mg/kg/day (and ordinarily greater than 2 mg/kg/day). If the intermediate form of the cHSNA is 50% bioavailable upon oral administration and is 3 times the molecular weight of the corresponding HSNA, then the oral dose of the cHSNA intermediate will be greater than about 6 mg/kg/day. The determination of bioavailability for such compounds is conventional and well within the ordinary skill in the art.

Alternatively, it will be within the skill of the ordinary artisan to determine the MND for other HPMPB or HSNA compounds by simply elevating the dosages until evidence of nephrotoxicity (2+ proteinuria) or other dose-limiting cytotoxicity is detected as described above. In general, initial dosages will be in the range of about 0.5 mg/kg to 10 mg/kg administered 1, 2 or 7 times a week, and thereafter the amounts are increased until toxicity is evident. Usually, only 1 or 2 animal species are studied, e.g., rats or guinea pigs, to arrive at non-cytotoxic candidate doses for humans in accord with conventional practice.

HSNA Intermediates

Included within the scope of this invention are intermediates for the cyclized HSNA compounds. Such intermediates have structure (VIIIa).

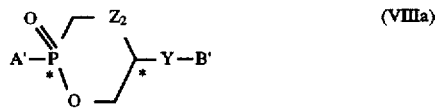

(VIIIa)

wherein $Z_2$, A, Y, *, and B' are defined above.

Suitable A substituents are amidates or esters which may, but need not be, hydrolyzable in vivo. Those which are not hydrolyzable in vivo are useful as intermediates for in vitro hydrolytic conversion to the free acids. Those that are hydrolyzable in vivo are useful as prodrugs. Group A includes $OD^1$ wherein $D^1$ is a saccharide residue, a glyceride lipid residue, unsubstituted $C_1$–$C_{20}$ alkyl (but usually not $C_1$–$C_2$ alkyl), $C_2$–$C_{20}$ alkenyl or alkynyl, $C_2$–$C_{10}$ alkyoxyalkyl, $C_4$–$C_{10}$ aryl, $C_4$–$C_{10}$ heteroaryl, $C_5$–$C_{20}$ alkaryl, $C_5$–$C_{20}$ alkoxyalkaryl, $C_5$–$C_{20}$ alkheteroaryl, —$CH_2C(O)NR_4$, —$CH_2C(O)OR_4$, —$CH_2OC(O)R_4$, —$CH(R_4)OC(O)R_4$, —$OC(R_4)HC(O)N(R_4)_2$, —$OC(R_4)HC(O)NH(R_4)$, —$CH_2C(R_4)_2CH_2OH$, or $C_5$–$C_{20}$ alkoxyalkheteroaryl groups, or the same groups in which at least one (ordinarily 1–3) hydrogen atom is substituted with amino, hydroxyl, carboxyl, —$OR_4$, —$COOR_4$, —$CON(R_4)_2$, —$CONH(R_4)$, —$CONH_2$, —$NO_2$, —$CX_3$, $OCX_3$, —$CN$, —$N_3$, or halo, where X is halo or hydrogen but at least one X is halo and $R^4$ is $C_1$–$C_{20}$ branched or normal alkyl, aryl or aralkyl which may be unsubstituted, or 1–3 hydrogen atoms of $R^4$ are independently substituted with hydroxy, amino or halogen.

For the purposes herein, alkyl groups are branched or normal, aryl groups contain two fused rings, or are monocyclic, and heteroaryl substituents contain 1 or 2 nitrogen atoms, an oxygen atom, an oxygen and a nitrogen atom, a sulfur atom, or a nitrogen and sulfur atom. Heteroatoms in aromatic rings with 2 ring heteroatoms ordinarily are separated by at least one methylene group.

Suitable esters $OD^1$ are disclosed in U.S. Ser. No. 08/123, 483 or EP 481,214. These include $D^1$=2,3-dihydro-6-hydroxyindene; sesamol; catechol monoester; $C_3$–$C_6$ aryl (e.g. phenyl); $C_3$–$C_6$ heteroaryl (including 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl and 2-, 4- and 5-pyrimidinyl); or such $C_3$–$C_6$ aryl or heteroaryl groups substituted by halogen (1–5 atoms), $C_1$–$C_{12}$ alkoxy (including methoxy and ethoxy) cyano, nitro, OH, $C_1$–$C_{12}$ haloalkyl (1 to 6 halogen atoms), $C_1$–$C_{12}$ alkyl (including methyl and ethyl), $C_2$–$C_{12}$ alkenyl or $C_2$–$C_{12}$ alkynyl. Other $D^1$ groups include $C_1$–$C_4$ alkyl- $C_3$–$C_6$-aryl (e.g. benzyl); $C_1$–$C_4$ alkyl-$C_3$–$C_6$-heteroaryl (including —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl); and such alkyl-$C_3$–$C_6$-aryl or -heteroaryl groups substituted at a hydrogen atom of the aryl or heteroaryl moiety by groups selected from halogen (1–5 atoms), $C_1$–$C_{12}$ alkoxy (including methoxy and ethoxy), cyano, nitro, OH, $C_1$–$C_{12}$ haloalkyl (1 to 6 halogen atoms), $C_1$–$C_{12}$ alkyl (including methyl and ethyl), $C_2$–$C_{12}$ alkenyl or $C_2$–$C_{12}$ alkynyl.

Exemplary $D^1$ groups include 2-, 3- and 4-alkoxyphenyl ($C_1$–$C_{12}$ alkyl) including 2-, 3- and 4-methoxyphenyl, 2-, 3- and 4-ethoxyphenyl; 2-, 3- and 4-carboethoxyphenyl; 2- and 3-carboethoxy-4-hydroxyphenyl; 2- and 3-ethoxy-4-hydroxyphenyl; 2- and 3-ethoxy-5-hydroxyphenyl; 2- and 3-ethoxy-6-hydroxyphenyl; 2-, 3- and 4-O-acetylphenyl; 2-, 3- and 4-dimethylaminophenyl; 2-, 3- and 4-methylmercaptophenyl; 2-, 3- and 4-halophenyl (including 2-, 3- and 4-fluorophenyl and 2-, 3- and 4-chlorophenyl); 2,3-, 2,4-, 2,5-, 2,6-, 3,4- and 3,5-dimethylphenyl; 2,3-, 2,4-, 2,5-, 2,6-, 3,4- and 3,5-biscarboxyethylphenyl; 2,3-, 2,4-, 2,5-, 2,6-, 3,4- and 3,5-dimethoxyphenyl; 2,3-, 2,4-, 2,5-, 2,6-, 3,4- and 3,5-diethoxyphenyl); 2,3-, 2,4-, 2,5-, 2,6-, 3,4- and 3,5-dihalophenyl (including 2,4-difluorophenyl and 3,5-difluorophenyl); 2-, 3- and 4-haloalkylphenyl (1 to 5 halogen atoms); 4-trifluoromethylphenyl; 2-, 3- and 4-cyanophenyl; 2-, 3- and 4-nitrophenyl; and 2-, 3- and 4-haloalkylbenzyl (1 to 5 halogen atoms), including 4 trifluoromethylbenzyl.

Acyloxymethyl esters (—$OCH_2OC(O)R^3$) or alkoxycarboxylmethyl esters (—$OCH_2C(O)OR^3$) are particularly useful. $R^3$ is $C_1$–$C_{15}$ (a) branched, normal or cycloalkyl, (b) unsubstituted monocyclic or polycyclic aryl or (c) either of the foregoing which are mono or disubstituted independently with —$OR^5$, —$R^5$, —$NO_2$, —$CX_3$, —$OCX_3$, or halo; $R^5$ is $C_1$–$C_5$ branched or normal alkyl; and X is defined above.

Exemplary A groups also include residues of α-D-galactose, α-D-glucose or α-D-fructose; enolpyruvate (HOOC-C(=CH$_2$)O—); glycerol; or D-α,β-diglyceride. The fatty acids composing glyceride lipids generally are naturally occurring saturated or unsaturated C$_6$-C$_{26}$ fatty acids such as linoleic, lauric, myristic, palmitic, stearic, oleic, palmitoleic, linolenic and the like fatty acids.

Group A also is an amidate, e.g. —NHR$^5$,—N(R$^5$)$_2$, —NHC(=NH)N(CH$_3$)CH$_2$COOH, or an amino acid residue or peptide, wherein R$^5$ is defined above. In the lattermost instance, an amino acid residue or peptide is linked to the phosphorus atom through an epsilon or alpha amino group, thereby producing a phosphoramidate bond. The amino acid residue is any moiety comprising at least one carboxyl and at least one amino residue linked by at least one intervening carbon atom, typically a single (α) carbon atom, while peptides are polymers of two or more of such amino acids.

A variety of intervening structures located between the carboxyl and amino (amidate) groups are suitable. All that is necessary is that the group have sufficient conformation and length to be capable of facilitating acid catalysis of the phosphoroamidate bond and release of the phosphonate by the carboxyl group. The free carboxyl generally is produced in vivo, e.g. by deesterification, deamidation or peptidolytic cleavage of a carboxyl ester or amide of the amino acid residue. In general, the intervening structure may be as simple as methylene (when the residue is glycyl) or substituted methylene (other α amino acids). The structure ordinarily contains up to about 5 carbon or heteroatoms in the direct linkage between the carboxyl carbon and the amidate nitrogen, as for example in the case of intervening ethylene, propylene, butylene, or pentylene groups or their substituted analogs, such as for example oxyesters in which O replaces carbon. An example of such an intervening structure would be —CH—O—CH(R$^7$)(R$^6$)—, where R$^6$ and R$^7$ are defined below. In general, fewer intervening atoms are employed when more rapid hydrolysis is desired, although it will be understood that larger structures are suitable if they possess sufficient flexibility or are capable of conformationally positioning the carboxyl group adjacent to the amidate bond.

In general, the amino acid residues for use herein have the structure shown in structure (IX).

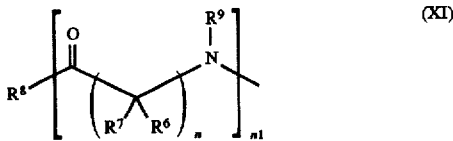

(XI)

Ordinarily, n is 1 or 2, R$^6$ is H and R$^7$ is a moiety containing one or more of the following groups: amino, carboxyl, amide, carboxyl ester, hydroxyl, C$_6$-C$_7$ aryl, ether, n-, s- or t-alkyl (C$_1$-C$_6$), guanidinyl, imidazolyl, indolyl, sulfhydryl, sulfoxide, and phosphoryl, or R$^7$ is taken together with R$^9$ to form C$_3$-C$_4$ alkylene when n=1. Other R$^7$ groups include 1-guanidinoprop- 3-yl, benzyl, 4-hydroxybenzyl, imidazol-4-yl, indol-3-yl, methoxyphenyl and ethoxyphenyl.

Ordinarily R$^6$ is H and R$^7$ is a side group or atom of a naturally occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$, —(CH$_2$)$_3$—[R$^9$], and —(CH$_2$)$_3$—NH—C(NH$_2$)—NH$_2$. With respect to the carboxyl-containing side chains of naturally occurring amino acids such as glutamic and aspartic acid, it will be understood that if the C atom of the amino acid carboxyl group is linked by 5 or less atoms to the phosphoramide N atom then the carboxyl will be blocked, e.g. by esterification or amidation.

R$^8$ is OD$^2$ or N(D$^2$)$_2$ wherein D$^2$ is independently H or D$^1$ described above, but ordinarily is H, unsubstituted C$_3$-C$_9$ alkyl, C$_1$-C$_5$ alkyl-O—C$_1$-C$_5$ alkyl, phenyl, C$_4$-C$_6$ cycloalkyl, or benzyl, or is C$_3$-C$_9$ alkyl, C$_1$-C$_5$ alkyl-O—C$_1$-C$_5$ alkyl, phenyl, C$_4$-C$_6$ cycloalkyl, or benzyl substituted with OH, N(D$^2$)$_2$, halogen, carboxyl, amide, or carboxyl ester (COOR$^4$).

R$^9$ is H or D$^2$, but usually is H.

When the amino acid residues contain one or more chiral centers, any of the D, L, meso, threo or erythro (as appropriate) racemates, or mixtures thereof are suitable. In general, if the HSNA intermediate is to be hydrolyzed non-enzymatically in vivo, D isomers should be used. On the other hand, L isomers may be more versatile since they can be susceptible to both non-enzymatic as well as potential targeted enzymatic hydrolysis, and may be more efficiently transported by amino acid or dipeptidyl transport systems in the gastrointestinal tract.

Examples of suitable amino acid residues include the following:

Glycyl;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues;

Amino acid amides such as glutaminyl and asparaginyl;

Polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric acid residues;

Other basic amino acid residues such as histidinyl;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues;

Amino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$COOR$^4$)$_2$, wherein n and R$^4$ are as defined above, and azetidine-2-carboxylic acid residues;

A mono- or di-alkyl (typically C$_1$-C$_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl;

Aliphatic α-amino-β-hydroxy acids such as serine, β-hydroxyleucine, β-hydroxynorleucine, β-hydroxynorvaline, and α-amino-β-hydroxystearic acid residues;

α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl;

2-hexosaminic acids such as D-glucosaminic acid or D-galactosaminic acid residues;

α-Amino-β-thiols such as penicillamine, β-thiolnorvaline or β-thiolbutyrine residues;

Other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine;

Phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4, 6-trimethyl-, 2-ethoxy-5-nitro, 2-hydroxy-5-nitro and p-nitrophenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues;

α-Amino substituted amino acid residues including sarcosine (N-methylglycine), N-benzylglycine, N-methylalanine, N-benzylalanine, N-methyphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any amino acid is suitably employed as an A group provided that it is capable of autocatalytically hydrolyzing the amidate bond. Thus, they must contain, or must, upon being converted (hydrolyzed) in vivo, a free carboxyl group. In general, the amino acids corresponding to the residues employed in the compounds of this invention are naturally occurring and have no pharmacological activity. However, optimal pharmacokinetic activity (substantially complete autocatalytic hydrolysis upon hydrolysis of the distal amide or ester bond) may be achieved by the use of non-naturally occurring amino acid residues.

Of particular interest are hydrophobic residues such as mono-or di-alkyl or aryl amino acids, cycloalkylamino acids (proline) and the like. These hydrophobic residues, together with $R^8$, contribute to cell permeability by increasing the partition coefficient of the nucleotide analog amidate. Typically, the residue will not contain a sulfhydryl or guanidino substituent.

If n1 is greater than 1, then Group A is a polypeptide radical, including dipeptides, short polypeptides of 3, 5 or 10 residues, or proteins having up to 100 or more residues. For the most part, dipeptides not containing aspartic or glutamic acid in the residue adjacent to the P atom will not autocatalytically hydrolyze the amidate bond and therefore the carboxyl groups (generally 1 or 2) in the distal residue do not need to be esterified or amidated, i.e., $R^8$ can be OH in these circumstances. However, if such compounds are intended to be used as precursors for the free phosphonate nucleotide analog in vivo, rather than as immunogens for example, the polypeptides ordinarily will contain a peptidolytic enzyme cleavage site at the peptide bond linking the first residue and the next residue distal to the phosphorus atom. Such cleavage sites are flanked by enzymatic recognition structures, e.g. particular residues recognized by a peptidolytic enzyme.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its ∝-amino group to the phosphorus atom of the HSNA's of this invention. It is expected that this peptide will be cleaved by the appropriate dipeptidase or protease, leaving the carboxyl of the proximal amino acid residue to autocatalytically cleave the amidate bond.

Examples of dipeptidyl groups (designated by their single letter code) include AA, AR, AN, AD, AC, AE, AQ, AG, AH, AL, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV, wherein the amidate bond is formed with the second residue.

Exemplary dipeptidyl A groups have the structure of formula (X) wherein $R^6$ is H, $R^7$ independently are the side chains of a naturally occurring amino acid, and $R^8$ and $R^9$ independently are as defined above.

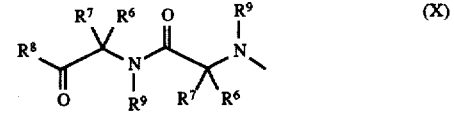

Tripeptides also are useful. The A group sequence —$X^1$Pro$X^2$ (where $X^1$ is any amino acid and $X^2$ is an amino acid, a carboxyl ester of Pro or H) will be cleaved by luminal carboxypeptidase to yield $X^1$ with a free carboxyl, which in turn autocatalytically cleaves the amidate bond. $X^2$ usually will be benzyl ester. Thus, n1 usually is 1, 2 or 3, but may range up to 5, 10 or 100 or more residues.

If the amino acid residue has 2 or more amine groups, e.g., in the case of lysinyl, arginyl or ornithinyl residues, then $R^7$ represents the group —[C(R$^{10}$)$_2$]$_{n2}$N(R$^6$)— where n2 is 0 to 6, $R^{10}$ is H, $C_1$–$C_{20}$ alkyl, $C_6$–$C_{20}$ aryl, $C_7$–$C_{20}$ alkylaryl, $C_7$–$C_{20}$ arylalkyl, $C_1$–$C_{20}$ alkoxy, $C_6$–$C_{20}$ aryloxy or hydroxyl, and $R^6$ is defined above. Such compounds will contain a plurality of phosphonate moieties. For example when both the epsilon (ε)/delta (δ) and alpha (α) amino groups of lysine or ornithine are substituted with HSNA moieties the amidate contains and is believed to be capable of releasing two molecules of active drug, each expected to emerge under different pharmacokinetics and therefore further sustaining the drug release.

The compounds herein may or may not exclude the compounds of structure (VIIIa) disclosed in EP 481,214. However, as noted above, the compounds herein include the cHPMB compounds (Formula V) of EP 481,214 wherein the stereochemistry at the phosphorous atom is (R) substantially free of (S) or (S) substantially free of (R).

Bases

Typically, B' is selected from structures (XI)–(XIV).

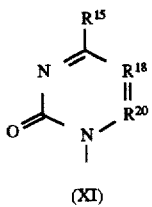
(XI)

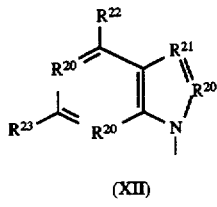
(XII)

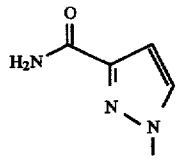
(XIII)

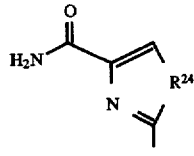
(XIV)

wherein $R^{15}$ is H, OH, F, Cl, Br, I, OR$^{16}$, SH, SR$^{16}$, NH$_2$, or NHR$^{17}$;

$R^{16}$ is $C_1$–$C_6$ alkyl including CH$_3$, CH$_2$CH$_3$, CH$_2$CCH (2-propynyl), CH$_2$CHCH$_2$ (2-allyl), C$_3$H$_7$;

$R^{17}$ is $C_1$–$C_6$ alkyl including CH$_3$, CH$_2$CH$_3$, CH$_2$CCH, CH$_2$CHCH$_2$, C$_3$H$_7$;

$R^{18}$ is N, CF, CCl, CBr, CI, CR$^{19}$ or CSR$^{19}$, COR$^{19}$;

$R^{19}$ is H, $C_1$–$C_9$ alkyl, $C_2$–$C_9$ alkenyl, $C_2$–$C_9$ alkynyl or $C_7$–$C_9$ aryl-alkyl unsubstituted or substituted by OH, O, N, F, Cl, Br or I including CH$_3$, CH$_2$CH$_3$, —CHCH$_2$, —CHCHBr, CH$_2$CH$_2$Cl, CH$_2$CH$_2$F, —CH$_2$CCH, —CH$_2$CHCH$_2$, C$_3$H$_7$, CH$_2$OH, CH$_2$OCH$_3$, CH$_2$OC$_2$H$_5$, —CH$_2$OCCH, —CH$_2$OCH$_2$CHCH$_2$, CH$_2$C$_3$H$_7$, CH$_2$CH$_2$OH, CH$_2$CH$_2$OCH$_3$, CH$_2$CH$_2$OC$_2$H$_5$, —CH$_2$CH$_2$OCCH, —CH$_2$CH$_2$OCH$_2$CHCH$_2$, CH$_2$CH$_2$OC$_3$H$_7$;

$R^{20}$ is N, CBr, CCl, CNH$_2$, C=N—NH$_2$, COH, CR$^{19}$, C=S, or CH;

$R^{21}$ is N, CH, CCN, CCF$_3$, CC≡CH or CC(O)NH$_2$;

$R^{22}$ is H, OH, NH$_2$, SH, SCH$_3$, SCH$_2$CH$_3$, SCH$_2$CCH, SCH$_2$CHCH$_2$, SC$_3$H$_7$, NH(CH$_3$), N(CH$_3$)$_2$, NH(CH$_2$CH$_3$), N(CH$_2$CH$_3$)$_2$, NH(CH$_2$CCH), NH(CH$_2$CHCH$_2$), NH(C$_3$H$_7$) or halogen (F, Cl, Br or I);

$R^{23}$ is H, OH, F, Cl, Br, I, SCH$_3$, SCH$_2$CH$_3$, SCH$_2$CCH, SCH$_2$CHCH$_2$, SC$_3$H$_7$, OR$^{16}$, NH$_2$, or NHR$^{17}$; and $R^{24}$ is O or S.

B' includes both protected and unprotected bases certain of which are described above. Protecting groups for exocyclic amines and other labile groups are known (Greene et al, "Protective Groups in Organic Synthesis") and include N-benzyl, isobutyryl, 4,4-dimethoxytrityl (DMT) and the like. The selection of protecting group will be apparent to the ordinary artisan and will depend upon the nature of the labile group and the chemistry which the protecting group is expected to encounter, e.g. acidic, basic, oxidative, reductive or other conditions. Exemplary protected species are N$^4$-benzoylcytosine, N$^6$-benzoyladenine, N$^2$-isobutyrylguanine and the like.

Exemplary bases include adenine, cytosine, guanine, hypoxanthine, inosine, thymine, uracil, xanthine, 2-aminopurine, 2,6-diaminopurine, 2-amino-6-chloropurine, 8-aza derivatives of adenine, guanine, 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 1-deaza derivatives of adenine, guanine, 2-aminopurine, 2,6-diaminopurine, 2-amino-6-chloropurine, hypoxanthine, inosine and xanthine; 7-deaza derivatives of adenine, guanine, 2-aminopurine, 2,6-diaminopurine, 2-amino-6-chloropurine, hypoxanthine, inosine and xanthine; 3-deaza derivatives of adenine, guanine, 2-aminopurine, 2,6-diaminopurine, 2-amino-6-chloropurine, hypoxanthine, inosine and xanthine; 6-azacytosine, 5-fluorocytosine, 5-chlorocytosine, 5-iodocytosine, 5-bromocytosine, 5-methylcytosine, 5-bromovinyluracil, 5-fluorouracil, 5-chlorouracil, 5-iodouracil, 5-bromouracil, 5-trifluoromethyluracil, 5-methoxymethyluracil, 5-ethynyluracil, 5-propynyluracil and the like.

Typical bases include adenine, 1-deazaadenine, 3-deazaadenine, 7-deaza-8-azaadenine, 8-azaadenine, guanine, 2, 6-diaminopurine, 2-aminopurine, cytosine, 6-azacytosine, 5-fluorocytosine, 5-methylcytosine, 5-bromovinyluracil, 5-fluorouracil and 5-trifluoromethyluracil.

In general, B' in the case of compounds of structure (VIIa) will have structure (XI), while B' will be one of structures (VIII), (VIIII) or (XIV) in structures (IIa), (IIIa), (VIa), (Ia), (Va) and (IVa).

Methods of Manufacture of HSNAs cHPMPC and the cyclic analogues of other HSNAs are prepared by a number of methods from the free hydroxy phosphonic acid. These methods include treatment with DCC in DMF (Ho et al., op cit.), reaction with Vilsmeier's reagent (ClCH=N(CH$_3$)$_2$Cl), or methods of phosphate activation known per se. In one embodiment of this invention for the preparation of cHSNA from the corresponding HSNA, the HSNA is (a) treated with ClCH=N(CH$_3$)$_2$Cl to yield the phosphonylchloridate and (b) optionally the phosphonylchoridate is reacted with a nucleophile (preferably at low temperature, e.g. lower than about −20° C.) such as an alcohol or amine to produce one of the intermediates described above. In a further step the product of steps (a) or (b) are subject to hydrolysis or protonolysis (typically acid protonolysis) respectively to yield the cHSNA (treatment of the product of step (a)) or its intermediate (treatment of the product of step (b)). Vilsmeier's reagent is advantageously produced in situ by combining SOCl$_2$, PCl$_5$, POCl$_3$, COCl$_2$ or the like with DMF. Advantageously, the product of step (a) is not purified or separated from the reaction mixture before being reacted with the nucleophile, a distinct economic advantage for this synthetic route. The compounds of structure (Ia) and (Va) are readily made from their uncyclized counterparts by the same methods, e.g. treatment with DCC in DMF.

Substituted and unsubstituted alkyl, aryl, heteroaryl, arylalkyl, heteroarylalkyl and other $D^1$ esters and amidates of cHSNA typically are made by reacting the appropriate HSNA with $SOCl_2/DMF$ to yield the activated phosphonylchloride (see Scheme 1), followed by treatment with the corresponding nucleophile (e.g. alkoxide, phenolate, amine, etc.) to yield the protected intermediate formamidine which is subsequently hydrolyzed to the target compound. Alternatively, esters can also be prepared as depicted in Scheme 2. The N-,O- protected intermediate phosphonate diester is obtained from the three building blocks by known methods. The N- and O- protecting groups are subsequently removed followed by treatment of the phosphonate diester 3 with NaH leading to cyclization yielding target compound 4. A third method for the synthesis of cHSNA esters entails alkylation of the cHSNA using common alkylating agents $D^1L$ (where L is a leaving group) such as alkyl halides, tosylates, diazoalkanes and the like (see Scheme 3). This method is particularly useful for preparing acyloxyalkyl esters by treatment of the cHSNA with the corresponding acyloxyalkylhalide. In an exemplary method for the preparation of acyloxyalkyl esters of cHSNAs, shown in more detail in Example 8, DCC and $R^4C(O)OCH_2Cl$ are reacted with the cHSNA; but in contradistinction with prior methods the stoichiometric proportion of DCC: $R^4C(O)OCH_2Cl$, cHSNA is 1–2:1–2:1. Use of such low proportions of reactants lessens side reactions with any exocyclic amino group of B' and thereby greatly improves yields.

Stereochemically pure compounds at the carbon chiral center are known or readily prepared by known methods. The general method exemplified in Example 7 is useful in preparing a substantially pure phosphorus atom enantiomer of the intermediate compounds herein. If the general method of Example 7 is not suitable to yield the desired enantiomer then the racemate is prepared and the enantiomers separated by conventional methods, e.g. chromatography. In general, this separation will be simplified if the carbon chiral center is a pure enantiomer obtained by judicious selection of appropriate starting materials, whereby only the phosphorus atom is racemic.

Each of the following schemes exemplify cytosine as the base. However, any B' is employed in place of cytosine, provided that any exocyclic oxo or amino groups are protected as required. Also, step 3 of scheme 1 obviously will be omitted when B' contains no exocyclic amine.

Scheme 1

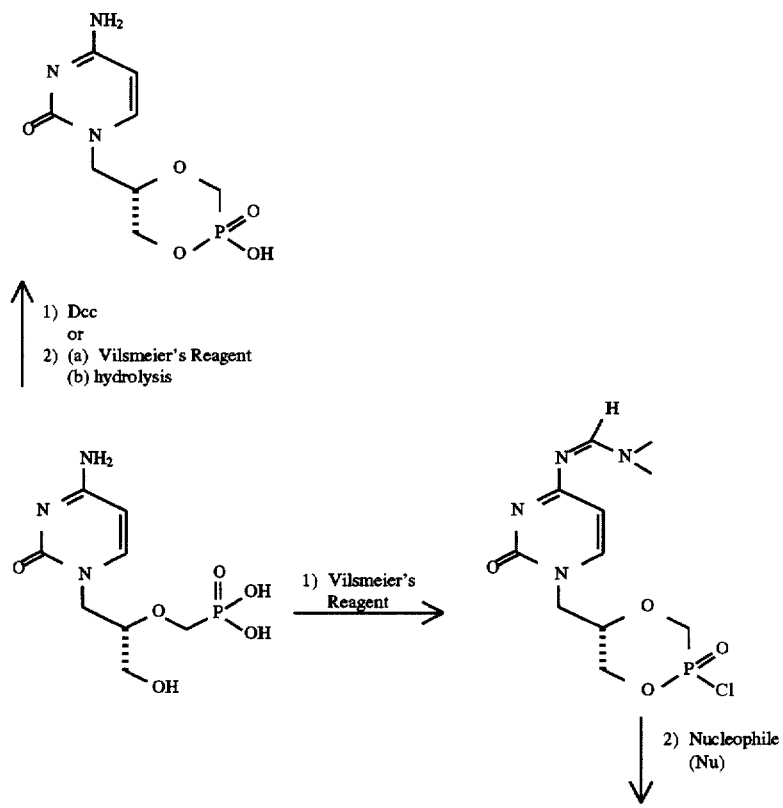

-continued
Scheme 1
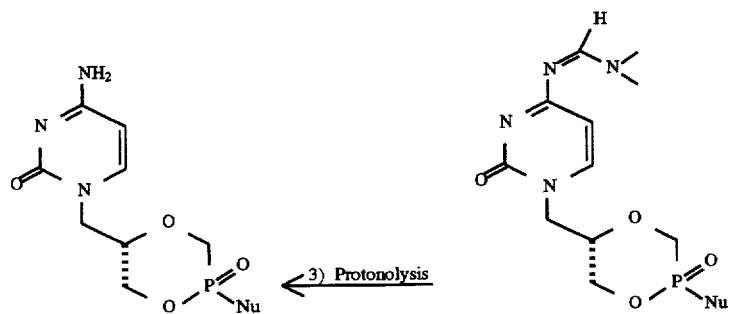
Scheme 2
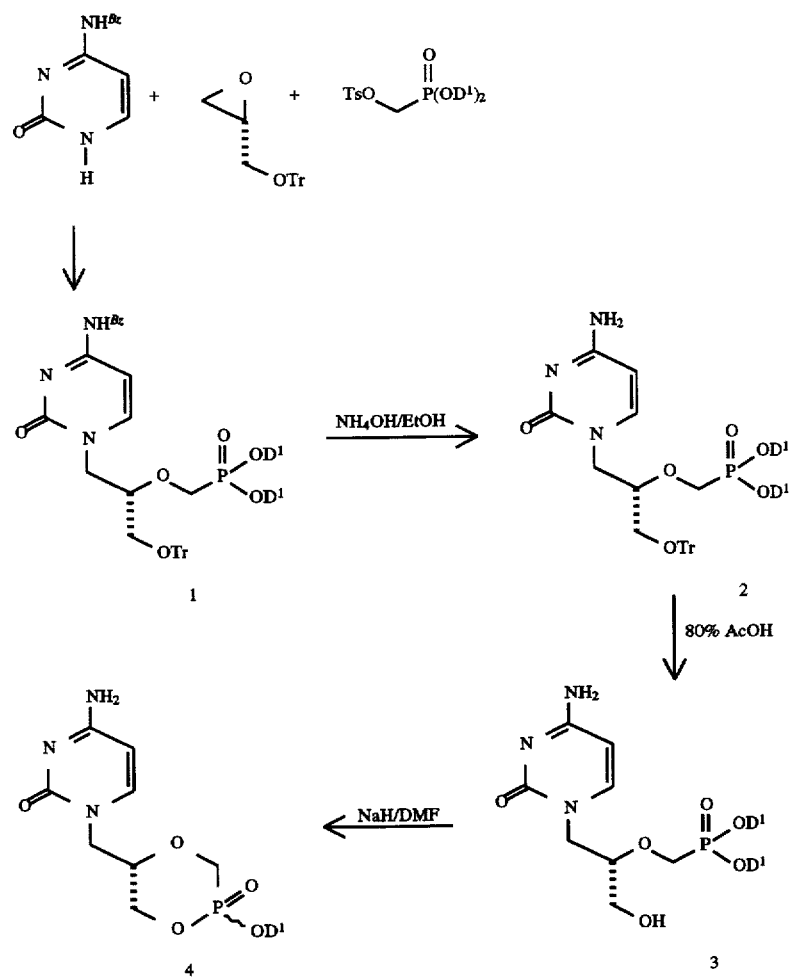

Scheme 3

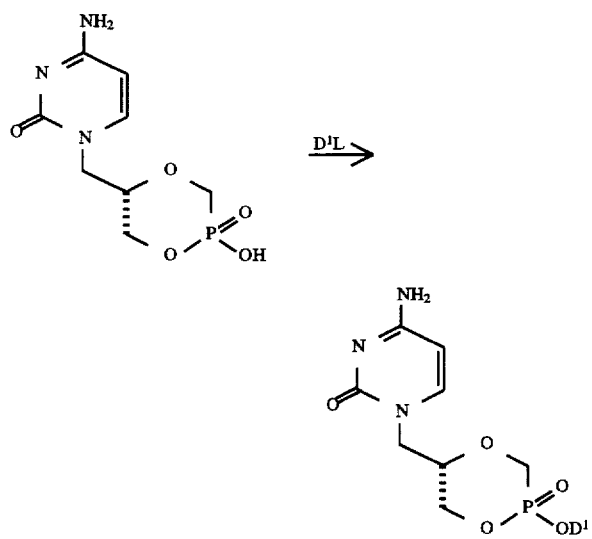

Salts

The compounds of this invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Pharmaceutically acceptable metal and amine salts are useful herein and include salts which are stable under ambient conditions and which contain nontoxic cations. Suitable metal salts include the sodium, potassium, calcium, barium, zinc, and aluminium salts. The sodium and potassium salts are preferred. Suitable amine salts are prepared from amines which have sufficient basicity to form a stable salt, and preferably include those amines which are frequently used in medicinal chemistry because of their low toxicity and acceptability for medical use. These include ammonium and the trialkylamines such as triethylamine, and others including procaine, dibenzylamine, N-benzyl-beta-phenethylamine, ephenamine, N,N'-dibenzylethylenediamine, dehydroabietylamine, N-ethylpiperidine, benzylamine, basic amino acids, e.g. lysine and arginine, and dicyclohexylamine.

Acid addition salts are formed with the compounds of the invention in which a basic function such as an amino, alkylamino, or dialkylamino group is present as a substituent on B'. The pharmaceutically acceptable, i.e., nontoxic, acid addition salts are preferred. They are chosen optimally to be compatible with the customary pharmaceutical vehicles and adapted for oral or parenteral administration. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, and others.

Pharmaceutical Formulations

Compounds of the invention and their pharmaceutically, i.e. physiologically, acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). It will be appreciated that the preferred route may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the patient.

The formulations include those suitable for topical or systemic administration, including oral, rectal, nasal, buccal, sublingual, vaginal or parenteral (including subcutaneous, intramuscular, intravenous, intradermal, intrathecal and epidural) administration. The formulations are in unit dosage form and are prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g. mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is suitably present in such formulations in a concentration of 0.01 to 20%, in some embodiments 0.1 to 10%, and in others about 1.0% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal or inhalational administration wherein the carrier is a solid include a powder having a particle size for example in the range 1 to 500 microns (including particle sizes in a range between 20 and 500 microns in increments of 5 microns such as 30 microns, 35 microns, etc). Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration are sterile and include aqueous and non-aqueous injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as recited above, or an appropriate fraction thereof, of an active ingredient.

In addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition to cats, dogs, horses, rabbits and other animals and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing a matrix or absorbent material and as active ingredient one or more compounds of the invention in which the release of the active ingredient can be controlled and regulated to allow less frequent dosing or to improve the pharmacokinetic or toxicity profile of the compound. Controlled release formulations adapted for oral administration in which discrete units comprising one or more compounds of the invention can be prepared according to conventional methods.

Anti-Infective Activity

The invention compounds are used in the treatment or prophylaxis of various microbial infections particularly human bacterial, human parasitic protozoan or human viral infections caused by microbial species including Plasmodium, Pneumocystis, herpesviruses (CMV, HSV 1, HSV 2, VZV, and the like), retroviruses, hepadnaviruses, (e.g. HBV), papillomavirus, hantavirus, adenoviruses and the like. The controlled release formulations can be used to treat HIV or HIV-related opportunistic infections and related conditions such as tuberculosis, malaria, pneumocystis pneumonia, and CMV retinitis. Other retroviral infections that may be treated with the compounds according to the invention include Human T-cell Lymphotropic virus (HTLV)-I and IV and HIV-2 infections, MSV, RSV, SIV, FIV, MuLV, and other retroviral infections of rodents and other animals.

The following examples are intended to illustrate the invention and are not to be construed as limiting the scope of the claims. All citations herein are expressly incorporated by reference.

EXAMPLE 1

5 Day Repeat Dose Toxicity Study of HPMPC, cHPMPC and EtHPMPC Administered Intravenously to Rats A histopathological evaluation was performed on the kidneys from thirty male and thirty female Sprague-Dawley rats. The purpose was to evaluate the potential nephrotoxicity in rats following repeated intravenous once-a-day administration of either HPMPC, cHPMPC or EtHPMPC (monoethylphosphonate ester of HPMPC) for five consecutive treatment days and a 10 day post dosing observation period. Comparison was made to rats receiving vehicle (sterile 0.9% Saline for injection, USP). Water was available ad lib to the rats. The rats were divided into the following six groups:

| Group | Test Article | Dose Level (mg/kg/day) | Animals on Study Male | Animals on Study Female |
|---|---|---|---|---|
| 1 | Vehicle[a] | 0.0 | 5 | 5 |
| 2 | HPMPC | 100.0 | 5 | 5 |
| 3 | cHPMPC | 100.0 | 5 | 5 |
| 4 | cHPMPC | 250.0 | 5 | 5 |
| 5 | EtHPMPC | 100.0 | 5 | 5 |
| 6 | EtHPMPC | 250.0 | 5 | 5 |

[a]Sterile 0.9% Saline for injection, USP.

Complete necropsies were performed on all of the animals and selected tissues were fixed and preserved in 10% neutral buffered formalin. Paraffin embedded, hematoxylin and eosin stained section of the kidneys were prepared by Experimental Pathology Laboratories, Inc. and evaluated from all of the animals.

Microscopic findings for each tissue examined from each animal are listed in the Histopathology Incidence Tables 3 and 4 below. Inflammatory, degenerative and hyperplastic changes were graded from one to five depending upon severity; nongradable changes were designated as present (P) in the Histopathology Incidence Tables. All lesions are summarized by treatment group and sex in the Summary Incidence Tables together with the total number of animals in each group for which the tissues were examined. The descriptions of the gross findings on these tables were transcribed from the Individual Animal Necropsy Sheets. Gross changes observed at the time of tissue processing are indicated as "(noted at gross trimming)".

Treatment related changes were present in the kidneys of the male and female rats receiving 100.0 mg/kg/day of HPMPC but not in the kidneys of the male or female rats receiving 100.0 and 250.0 mg/kg/day of cHPMPC or 100.0 and 250.0 mg/kg/day of EtHPMPC. These kidney changes in the rats receiving 100.0 mg/kg/day of HPMPC were characterized by a minimal to moderately-severe tubular depletion and degeneration accompanied by a minimal to moderate tubular cytomegaly and tubular karyomegaly and minimal to moderately-severe tubular regeneration of the outer cortical tubules. In the more severely affected kidneys there was a loss of renal tubules in the outer cortical region. There were little or no inflammatory changes in these kidneys. The kidney changes were more severe in the males than in the females.

TABLE 3

SUMMARY INCIDENCE
Terminal Sacrifice
Male Rat

| | GROUP 1 | GROUP 2 | GROUP 3 | GROUP 4 | GROUP 5 | GROUP 6 |
|---|---|---|---|---|---|---|
| KIDNEY (NO. EXAMINED) | (5) | (5) | (5) | (5) | (5) | (5) |
| Congestion | 4 | | 4 | 2 | 2 | 5 |
| Cyst(s) Cortical | 1 | | 1 | 1 | 1 | |
| Mononuclear Cells | | 5 | 1 | | | 1 |
| Nephritis, Nonsuppurative, Multifocal | 3 | | 2 | 4 | 1 | 1 |
| Nephritis, Subacute, Multifocal | | 3 | | | | |
| Pelvic Dilatation, Bilateral | 1 | | 1 | | | |
| Pelvic Dilatation, Unilateral | 1 | | 1 | | | |
| Tubular Basophilia | | 2 | | | | |
| Tubular Cytomegaly | | 5 | | | | |
| Tubular Depletion/ Degeneration | | 5 | | | | |
| Tubular Dilatation | 1 | 5 | | 1 | 1 | 1 |
| Tubular Karyomegaly | | 5 | | | | |
| Tubular Mineralization | | | | | | |
| Tubular Regeneration | 3 | 5 | 4 | 5 | 3 | 1 |

TABLE 4

SUMMARY INCIDENCE
Terminal Sacrifice
Female Rat

| | GROUP 1 | GROUP 2 | GROUP 3 | GROUP 4 | GROUP 5 | GROUP 6 |
|---|---|---|---|---|---|---|
| KIDNEY (NO. EXAMINED) | (5) | (5) | (5) | (5) | (5) | (5) |
| Congestion | 3 | 2 | 4 | 3 | 4 | 4 |
| Cyst(s), Cortical | | | 1 | 1 | 1 | |
| Mononuclear Cells | | 5 | 1 | 1 | | |
| Nephritis, Nonsuppurative, Multifocal | 1 | 1 | 2 | 2 | 1 | 1 |
| Nephritis, Subacute, Multifocal | | | | | | |
| Pelvic Dilatation, Bilateral | | | | | | |
| Pelvic Dilatation, Unilateral | 1 | | | 1 | 1 | |
| Tubular Basophilia | | 5 | | | | |
| Tubulat Cytomegaly | | 4 | | | | |
| Tubular Depletion/Degeneration | | 4 | | | | |
| Tubular Dilatation | | 3 | 1 | | | |
| Tubular Karyomegaly | | 4 | | | | |
| Tubular Mineralization | 3 | 2 | 1 | | | 2 |
| Tubular Regeneration | 3 | 5 | 2 | 2 | 2 | 1 |

Incidental changes in the kidneys of a few control and treated rats had changes compatible with the early microscopic changes of old rat nephropathy. These microscopic changes consisted of one or more of the following: multifocal nonsuppurative nephritis, tubular dilatation and/or tubular regeneration. Additional incidental kidney lesions were unilateral or bilateral pelvic dilatation.

A few microscopic findings were observed in the kidneys of individual rats and occurred as incidental findings or in such small numbers as to have no apparent relationship to the test material. These changes were of the usual number, type and frequency observed in this strain and their presence did not interfere with the evaluation of the test material used in this study.

EXAMPLE 2

14-Day Intravenous Toxicity Study of cHPMPC in Rats

A histopathological evaluation was performed on selected tissues from twenty male and twenty female Sprague-Dawley rats. The purpose was to evaluate the potential systemic toxicity of cHPMPC in rats following repeated intravenous administration (once-a-day) over a 14 day treatment period. Comparison was made to rats receiving vehicle (0.9% Saline). Water was available ad lib to the rats. The rats were divided into the following four groups:

| Group | Test Article | Dose Level (mg/kg/day) | Animal Study Male | Animal Study Female |
|---|---|---|---|---|
| I | Vehicle* | 0.0 | 5 | 5 |
| II | cHPMPC | 10.0 | 5 | 5 |
| III | cHPMPC | 40.0 | 5 | 5 |
| IV | cHPMPC | 150.0 | 5 | 5 |

*0.9% Saline.

Complete necropsies were performed on all of the animals and selected tissues were fixed and preserved in 10% neutral buffered formalin. Paraffin embedded, hematoxylin and eosin stained sections of the following tissues were prepared by Experimental Pathology Laboratories, Inc. from the rats in groups I and IV: esophagus, intestine, large (cecum, colon and rectum), intestine, small (duodenum, jejunum and ileum), liver, lymph nodes (mesenteric), ovaries (female), spleen, stomach, testes (male), urinary bladder and injection site. The kidneys and liver were processed and evaluated from the rats in Groups II and III.

Treatment related changes were present in the kidneys of the male and female rats receiving 40 and 150 mg/kg/day of cHPMPC but not in the kidneys of the male or female rats receiving 10 mg/kg/day of cHPMPC. The kidney changes were more severe in the males than in the females. No treatment related lesions were present in the esophagus, large intestine, liver, mesenteric lymph nodes, ovaries, spleen, small intestine, stomach, testes, urinary bladder or injection site in the male and female rats receiving 150 mg/kg/day of cHPMPC for 14 days. The toxic dose in this 14-day study was lower than in the 5-day study due to the length of therapy.

The kidney changes in the rats receiving 150 mg/kg/day of cHPMPC were characterized by a minimal to moderately-severe tubular depletion and degeneration accompanied by a minimal to moderate tubular cytomegaly and tubular karyomegaly and an increased incidence and/or severity of tubular regeneration and/or tubular dilatation. In the more severely affected kidneys there was a loss of renal tubules in the outer cortical region. Little or no inflammatory changes were present in these kidneys. In the rats receiving 40 mg/kg/day of cHPMPC, there was a minimal tubular cytomegaly and tubular karyomegaly in two males and an increased incidence of tubular regeneration in the females. These changes in the kidneys are summarized in Table 5.

TABLE 5

| TREATMENT | Vehicle | | GS930 | | | | | |
|---|---|---|---|---|---|---|---|---|
| GROUP | I | | II | | III | | IV | |
| DOSE (mg/kg/day) | 0 | | 10.0 | | 40.0 | | 150.0 | |
| NUMBER EXAMINED/SEX | 5M | 5F | 5M | 5F | 5M | 5F | 5M | 5F |
| Tubular Depletion/Degeneration (No.) | (0) | (0) | (0) | (0) | (0) | (0) | (5) | (5) |
| Minimal | | | | | | | | 5 |
| Slight | | | | | | | | 2 |
| Moderate | | | | | | | | 2 |

TABLE 5-continued

| | | | | | | | | |
|---|---|---|---|---|---|---|---|---|
| Moderately severe | | | | | | | 1 | |
| Tubular Cytomegaly (No.) | (0) | (0) | (0) | (0) | (2) | (0) | (5) | (5) |
| Minimal | | | | | 2 | | | 5 |
| Slight | | | | | | | 2 | |
| Moderate | | | | | | | 2 | |
| Moderately severe | | | | | | | 1 | |
| Tubular Karyomegaly (No.) | (0) | (0) | (0) | (0) | (2) | (0) | (5) | (5) |
| Minimal | | | | | 2 | | | 5 |
| Slight | | | | | | | 2 | |
| Moderate | | | | | | | 2 | |
| Moderately severe | | | | | | | 1 | |
| Tubular Dilatation (No.) | (1) | (1) | (1) | (0) | (1) | (0) | (5) | (3) |
| Minimal | 1 | 1 | | | | | 2 | 3 |
| Slight | | | 1 | | 1 | | 1 | |
| Moderate | | | | | | | 1 | |
| Moderately severe | | | | | | | 1 | |
| Tubular Regeneration (No.) | (2) | (3) | (2) | (1) | (1) | (5) | (5) | (4) |
| Minimal | 1 | 2 | 1 | 1 | 1 | 5 | 4 | 3 |
| Slight | 1 | 1 | 1 | | | | | 1 |
| Moderate | | | | | | | 1 | |

Incidental changes were present in the kidneys of a few control and cHPMPC treated rats. These microscopic changes consisted of one or more of the following: congestion, cortical cysts, mononuclear cells, multifocal nonsuppurative nephritis, tubular dilatation and/or regeneration, tubular mineralization and unilateral or bilateral pelvic dilatation.

Incidental changes were present in the livers of the control and cHPMPC treated rats. The more common of these were congestion, multifocal hepatocellular degeneration (single cell necrosis), multifocal nonsuppurative hepatitis, pericholangeal mononuclear cells and multifocal hepatocellular vacuolation. Although no treatment related changes were present in the livers of the male and female rats receiving 10, 40 and 150 mg/kg/day of cHPMPC the severity of the incidental changes was slightly higher in the rats receiving cHPMPC.

A variety of microscopic findings were observed in individual rats and occurred as incidental findings or in such small numbers as to have no apparent relationship to the test material. The degree of hematopoiesis in the spleens varied in the individual rats within groups and between sexes but was considered to be within normal limits for the age and strain of rats. The testes of the control males and the males receiving 150 mg/kg/day of cHPMPC had normal spermatogenesis. The ovaries of the control females and females receiving 150 mg/kg/day of cHPMPC had normal follicular activity. A few additional findings were observed in individual rats and occurred as incidental findings or in such small numbers as to have no apparent relationship to the test material. These were of the usual type and incidence seen in rats.

The incidental findings occurred in both treated and control rats at essentially comparable incidence and severity and were of the usual type and incidence commonly seen in rats. The presence of the incidental lesions did not interfere in the evaluation of the intravenous administration of cHPMPC, as used in this study.

These results with cHPMPC at 40 mg/kg/day compare quite favorably with, and are comparable to, the results with Sprague-Dawley rats using only 3 mg/kg/day of HPMPC by iv injection for 14 consecutive days (male rats only, 5 per group) as shown below in Tables 6a and 6b.

TABLE 6a

| | HPMPC (mg/kg/day) | | | |
|---|---|---|---|---|
| | Control (Saline) Group 5 | 0.3 Group 6 | 1.0 Group 7 | 3.0 Group 8 |
| Kidney | (5) | (5) | (5) | (5) |
| Focal interstitial nephritis | 5 | 5 | 5 | 2 |
| minimal | 5 | 5 | 5 | 2 |
| Inflammatory infiltrate | 0 | 0 | 0 | 4 |
| minimal | 0 | 0 | 0 | 3 |
| slight | 0 | 0 | 0 | 1 |
| Tubular nephrosis | 0 | 0 | 0 | 5 |
| slight | 0 | 0 | 0 | 2 |
| moderate | 0 | 0 | 0 | 2 |
| marked | 0 | 0 | 0 | 1 |

TABLE 6b

| | HPMPC 10 mg/kg Group 1 | HPMPC 50 mg/kg Group 2 |
|---|---|---|
| Kidney | (5) | (5) |
| Dilated tubule(s) | 0 | 0 |
| Focal interstitial nephritis | 0 | 0 |
| Inflammatory infiltrate | 5 | 5 |
| minimal | 0 | 2 |
| slight | 5 | 3 |
| Tubular nephrosis | 5 | 5 |
| marked | 3 | 0 |
| severe | 2 | 5 |

EXAMPLE 3

Efficacy of HPMPC, cHPMPC and EtHPMPC Against HSV-2 Encephalitis Infection in Mice In a preliminary study the antiviral activities of HPMPC, cHPMPC and EtHPMPC against herpes simplex virus type 2 (HSV-2) encephalitis infection in mice were evaluated. In that study the efficacies of the three compounds were very similar using doses of 3,1, 0.3 and 0.1 mg/kg/day. However, the overall infection was mild since only 50% of placebo-treated mice died. Because of the low mortality rate, this cast some doubt as to the validity of the results with respect to the relative potencies of these compounds. For this reason the present study was conducted whereby the virus challenge dose was adjusted to cause a more severe infection. This time it appeared that two of the compounds, HPMPC and cHPMPC, were similar in protective activity, and EtHPMPC was poorly active if not inactive.

Compounds: HPMPC, cHPMPC, and EtHPMPC were supplied in dry powder form. They were made up in sterile saline for intraperitoneal (i.p.) administration and stored frozen between treatments. Sterile saline served as the placebo control.

Infection: Swiss Webster female mice (Simonsen Labs, Gilroy Calif.) weighing approximately 17 grams each at the start of the experiment were infected i.p. with HSV-2 (MS strain) at $2 \times 10^5$ plaque forming units (PFU) per mouse. This differs from the preliminary experiment where the mice weighed approximately 20 grams each and received $1 \times 10^5$ PFU of virus. This slight adjustment in methodology was important to improve the percentage of mortality in placebo-treated mice.

Treatment: Three hours after virus inoculation, i.p. treatments with compounds and placebo were begun. Treatments were once daily for 5 days.

Parameters used to evaluate the infection: These included death and mean day to death determinations. Deaths were recorded daily for 21 days. The mean day of death calculation took into account only mice that died. Statistical interpretations of survival (Fisher Exact Test) and mean day to death (Mann Whitney U-Test) were made by two-tailed analyses.

Table 7 shows the results of the experiment, indicating that HPMPC was significantly effective in reducing mortality at 1 and 3 mg/kg/day, with lower doses being ineffective. Likewise, cHPMPC caused significant reductions in mortality at 1 and 3 mg/kg/day. EtHPMPC proved to be inactive at the doses tested. Only HPMPC at 0.3 mg/kg/day caused a significant increase in the mean day to death of mice that died, although doses of 1 and 3 mg cHPMPC/kg/day appeared to extend the life span.

TABLE 7

Effect of Three Antiviral Substances on HSV-2 (MS Strain) Included Encephalitis in Mice

| Compound | Dose[a] (mg/kg/day) | Survivors/ Total (%) | Mean Day to Death |
|---|---|---|---|
| HPMPC | 3 | 10/10 (100)** | >21 |
| HPMPC | 1 | 9/10 (90)** | 9.0 ± 0.0 |
| HPMPC | 0.3 | 3/10 (30) | 10.9 ± 2.3* |
| HPMPC | 0.1 | 3/10 (30) | 10.9 ± 4.8 |
| cHPMPC | 3 | 8/10 (80)** | 14.0 ± 4.2[b] |
| cHPMPC | 1 | 8/10 (80)** | 18.0 ± 28[b] |
| cHPMPC | 0.3 | 3/10 (30) | 11.0 ± 3.1 |
| cHPMPC | 0.1 | 0/10 (0) | 9.8 ± 2.3 |
| EtHPMPC | 3 | 3/10 (30) | 10.0 ± 2.0 |
| EtHPMPC | 1 | 1/10 (10) | 10.0 ± 2.1 |
| EtHPMPC | 0.3 | 1/10 (10) | 8.8 ± 1.6 |
| EtHPMPC | 0.1 | 2/10 (20) | 8.5 ± 1.4 |
| Placebo | — | 3/30 (10) | 8.8 ± 1.3 |

[a]Intraperitoneal treatments were once daily for 5 days starting 3 hours after virus challenge.
[b]Although these values appear to be statistically significant, there are too few data points for analysis.
*P < 0.05, **P < 0.001.

The foregoing examples unexpectedly demonstrate that cHPMPC is up to about 13-fold less toxic than its uncyclized congener, HPMPC, but is quite similar in its antiviral activity. We expect that similar effects will be observed for other HSNAs as well.

EXAMPLE 4 cHPMPC was synthesized by adding to a stirred suspension of HPMPC (100 g, 0.358 mol) in DMF (2L) N,N'-dicyclohexyl-4-morpholine-carboxamidine (115 g, 0.393 mol). The reaction mixture was stirred for 12 hours at room temperature. This solution was added slowly to a hot pyridine solution (5 L, 60° C.) of DCC (185 g, 0.895 mol) through an addition funnel. The reaction mixture was stirred at 100° C. for 16 hours, cooled to room temperature and the solvents were removed under reduced pressure. The crude mixture was washed with diethyl ether (3 L), dissolved in water (2 L) and washed with $CH_2Cl_2$ (5×1 L). The aqueous layer was concentrated to 1 L volume and acidified to pH-3.5. Upon cooling cyclic-HPMPC crystallized (89 g, ~95% pure). The cHPMPC was recrystallized by dissolving in water at pH8 (with 1N NaOH) followed by acidification to pH 3.5 (with 1N HCl):

CHN Analysis: cHPMPC monohydrate, monosodium salt. $C_8H_{11}N_3O_5PNa.H_2O$: theory: C31.90 H4.69 N13.96%; found: C32.39 H4.91 N13.95%; 32P-NMR: 9.35(s) (reference $H_3PO_4$); 1H-NMR: 3.70–4.27 (m, 7H), 4.80 (s,HDO), 6.15 (d, J=7.8, 1H), 7.83 (d, J=7.8, 1H). 13C NMR (75 MHz, $D_2O$) d, 169.4 s (4-C), 161.0 s (2-C), 150.2 s (6-C), 98.21 s (5-C), 76.86 d (JP,C=3.6 Hz, 2'—$CH_2$), 72.44 d (JP,C=6.3 Hz, 3'—$CH_2$), 67.88 d (JP,C=143.0 Hz, P-$CH_2$), 51.90 s (1'-C).

EXAMPLE 5 cHPMPU was synthesized by adding thionyl chloride (60 mL, 0.812 mmol, 2.02 eq) dropwise to a suspension of disodium HPMPU (131 mg, 0.404 mol) in N,N-dimethylformamide (1.25 mL) at ambient temperature. The resulting light-yellow solution was stirred for 20 min at ambient temperature and then concentrated to dryness (in vacuo, 45° C.). $H_2O$ (2 mL) was added and the resulting solution was concentrated to dryness. Methanol (4 mL) was added and the resulting solution was concentrated to dryness to afford the crude product as a light-yellow solid. Purification by silica flash chromatography (mobile phase: 30% methanol: 70% $CH_2Cl_2$ gradient to 50% methanol: 50% $CH_2Cl_2$) afforded pure cHPMPU in 69% yield as a white amorphous solid. 1H NMR (300 MHz, $D_2O$) d 7.62 d (1H, J=7.1 Hz, CH=CH), 5.82 d (1H, J=7.8 Hz, CH=CH), 4.30–3.71 m (7H, $CH_2CH(OCH_2P)CH_2OH$), NH and OH not observed in $D_2O$. 13C NMR (75 MHz, $D_2O$) d, 169.6 s (4-C), 155.1 s (2-C), 150.4 s (6-C), 104.2 s (5-C), 76.71 d (JP,C=3.6 Hz, 2'—$CH_2$), 72.30 d (JP,C=6.2 Hz, 3'—$CH_2$), 67.90 d (JP,C=142.0 Hz, P—$CH_2$), 50.71 s (1'-C). 31P NMR (121 MHz, $D_2O$) d 9.23 s.

EXAMPLE 6

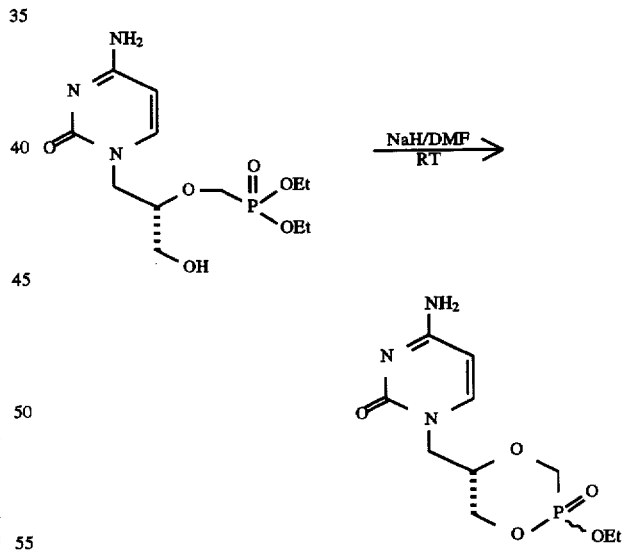

To a stirred solution of diethyl HPMPC (1.1 g) in DMF, NaH (115 mg) was added. After 15 min, the reaction mixture was quenched with acetic acid (1 eq). The solvents were removed under reduced pressure. The crude mixture was dissolved in $CH_2Cl_2$ and water. The organic layer was washed with NaCl solution and the crude material obtained was purified on a silica gel column (elution with 5%–10% MeOH in $CH_2Cl_2$) to get cyclic ethyl HPMPC (950 mg) as a diastereomeric mixture (approximately 70%).

EXAMPLE 7

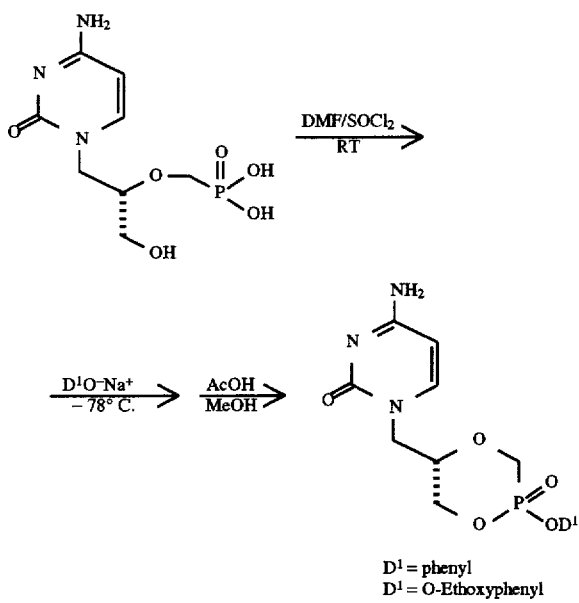

To a stirred suspension of HPMPC (2.79 g) in DMF, thionylchloride (2.1 mL) was added dropwise under anhydrous conditions and the mixture was stirred for 1 hr. In another flask, sodium aryloxide (using the appropriate aryl substituent) was made using the corresponding phenol (8.9 g) and NaH (1.8 g) in 1:1 DMF/THF (50 mL). This solution was cooled to −78° C. and the chloridate solution was added dropwise under anhydrous conditions. After 2 hrs, the reaction mixture was quenched with acetic acid (5 eq) and the solvents were evaporated under vacuum. The crude mixture was partitioned between water and $CH_2Cl_2$. The organic layer was concentrated and the residue was purified on a silica gel column (elution with 5%-10% MeOH in $CH_2Cl_2$) to get the cyclic aryl compound as a single diastereomer in approximately 60% yield. This method is suitable for all substituted or unsubstituted D' groups, especially aryl, subject of course to conventional protection of labile groups other than amino for which reaction is undesired (amino is protected by reaction with DMF and deprotected with acetic acid and alkanol treatment). This method offers the advantages of producing substantially stereochemically pure product, superior yield and ease of synthesis.

EXAMPLE 8

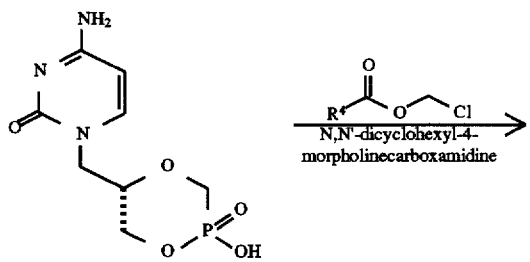

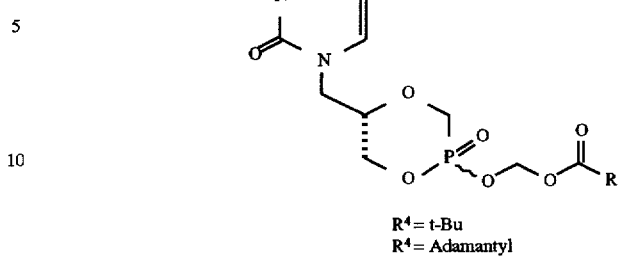

To a stirred suspension of cyclic HPMPC (1 mmol) was added N,N'-dicyclohexyl-4-morpholinecarboxamidine (2 mmol) followed by the corresponding acyloxymethyl chloride (1.5 mmol). The reaction was stirred for 3 days and the DMF was evaporated under reduced pressure. The crude was purified on a silica gel column (eluted with 5% methanol in methylene chloride) to get the pure cyclic HPMPC derivatives (approximately 30% yield).

We claim:

1. A compound of structure (1a)

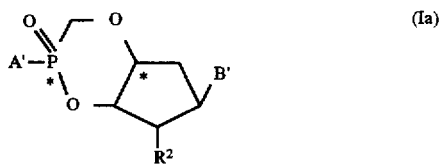

wherein * independently designates (S), (R) or (R,S) configuration;

B' a 9-purine heterocyclic ring structure;

$R^2$ is hydrogen, hydroxy, fluorine, chlorine, bromine, amino, or an organic substituent having 1–5 carbon atoms and selected from acyloxy, alkoxy, alkylthio, alkylamino or dialkylamino;

A' is OH or A; and

A is the residue of an amidate or ester;

and the salts thereof.

2. The compound of claim 1 wherein the carbon atom * chiral center is stereochemically pure as the (S) enantiomer.

3. The compound of claim 1 wherein B' is adenine, 2,6 diaminopurine, guanine.

4. A compound of structure (Va)

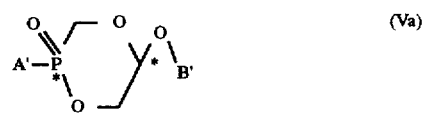

wherein * independently designates (S), (R) or (R,S) configuration;

A' is OH or A;

A is the residue of an amidate or ester;

B' is a 9-purine heterocyclic ring structure;

and the salts thereof.

5. The compound of claim 4 wherein the carbon atom * chiral center is stereochemically pure as the (S) enantiomer.

6. The compound of claim 4 wherein B' is adenine, 2,6 diaminopurine, guanine.

* * * * *

UNITED STATES PATENT AND TRADEMARK OFFICE
CERTIFICATE OF CORRECTION

PATENT NO. : 5,756,486

DATED : 5/26/98

INVENTOR(S) : Alexander et al.

It is certified that error appears in the above-identified patent and that said Letters Patent is hereby corrected as shown below:

On the title page,

Item [54] should read --Therapeutic Compounds--.

Signed and Sealed this

Twenty-third Day of March, 1999

Attest:

Q. TODD DICKINSON

Attesting Officer     Acting Commissioner of Patents and Trademarks

UNITED STATES PATENT AND TRADEMARK OFFICE
CERTIFICATE OF CORRECTION

PATENT NO: 5,756,486
DATED: : May 26, 1998
INVENTORS: Petr Alexander, Murty Arimilli, Norbert Bischofberger, Michael J. M. Hitchcock It is certified that error in the above-identified patent and that said Letters Patent is hereby corrected as shown below:

In Column 14, line 20 change "AL" (first occurrence) to --AI--.

Signed and Sealed this

Second Day of May, 2000

Attest:

Q. TODD DICKINSON

*Attesting Officer*                *Director of Patents and Trademarks*